US008333880B2

(12) United States Patent
Chang et al.

(10) Patent No.: US 8,333,880 B2
(45) Date of Patent: Dec. 18, 2012

(54) METHOD FOR DETECTING DISEASE MARKERS

(75) Inventors: Frank N. Chang, Dresher, PA (US); Phu T. Duong, Malvern, PA (US); George P. Tuszynski, Pittsgrove, NJ (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 224 days.

(21) Appl. No.: 12/670,343

(22) PCT Filed: Jan. 15, 2008

(86) PCT No.: PCT/US2008/000509
§ 371 (c)(1),
(2), (4) Date: May 12, 2010

(87) PCT Pub. No.: WO2009/014552
PCT Pub. Date: Jan. 29, 2009

(65) Prior Publication Data
US 2011/0031122 A1 Feb. 10, 2011

Related U.S. Application Data

(60) Provisional application No. 60/962,081, filed on Jul. 26, 2007.

(51) Int. Cl.
*G01N 27/447* (2006.01)
(52) U.S. Cl. ........................................ 204/546; 204/469
(58) Field of Classification Search .......... 204/605–618, 204/456–467, 546, 641, 469
See application file for complete search history.

(56) References Cited

U.S. PATENT DOCUMENTS

| | | | |
|---|---|---|---|
| 3,930,973 A | 1/1976 | Nerenberg | 204/546 |
| 3,984,298 A | 10/1976 | Haber | 204/456 |
| 4,128,470 A | 12/1978 | Hiratsuka et al. | 204/341 |
| 4,146,454 A | 3/1979 | Haber | 204/341 |
| 4,892,814 A * | 1/1990 | Harrington et al. | 435/5 |
| 4,909,918 A | 3/1990 | Bambeck et al. | 204/619 |
| 5,068,019 A | 11/1991 | Yoshida et al. | 204/546 |
| 5,137,609 A | 8/1992 | Manian et al. | 204/452 |
| 5,264,098 A | 11/1993 | Chevigné | 204/461 |
| 5,314,595 A | 5/1994 | Fuller | 204/468 |
| 5,637,202 A | 6/1997 | Harrington et al. | 204/469 |

(Continued)

FOREIGN PATENT DOCUMENTS

| | | |
|---|---|---|
| JP | 63-262550 A | 10/1988 |
| JP | 06-130033 A | 5/1994 |
| WO | 03/044485 | 5/2003 |

OTHER PUBLICATIONS (With English Translation)Heon-Chul Hong et al., "Protein Migration Using Organic Solvent in Filter Paper Electrophoresis Bath," *Journal of the Korean Institute of Chemical Engineers*, Hwahak Konghak, vol. 29, No. 4, Aug. 1991, pp. 457-462.

(Continued)

*Primary Examiner* — Alex Noguerola
(74) *Attorney, Agent, or Firm* — Drinker Biddle & Reath LLP

(57) ABSTRACT

Disease specific markers, in particular cancer markers, can be detected by electrophoretically separating proteins and protein complexes from a biological sample on a protein binding polymeric membrane in a low conductivity, water-miscible organic solvent buffer. Electrophoretic separation profiles representing different diseases can be produced, and used in the diagnosis or prognosis of these diseases.

32 Claims, 11 Drawing Sheets

U.S. PATENT DOCUMENTS

| | | | |
|---|---|---|---|
| 6,528,640 B1* | 3/2003 | Beigelman et al. | 536/25.1 |
| 6,855,554 B2* | 2/2005 | Fritsche et al. | 436/64 |
| 7,326,326 B2 | 2/2008 | Chang et al. | 204/546 |
| 7,575,858 B2 | 8/2009 | Yonan et al. | 435/4 |
| 2004/0121488 A1* | 6/2004 | Chang et al. | 436/517 |
| 2006/0068452 A1 | 3/2006 | Goldknopf et al. | |
| 2007/0161030 A1 | 7/2007 | Patton | |

OTHER PUBLICATIONS

Michael Lederer, "An Introduction to Paper Electrophoresis and Related Methods," Elsevier Publishing Company, 1955, pp. 23-30.

Allen, et al., "Hybrid (BDBB) interferon-$\alpha$: preformulation studies," *International Journal of Pharmaceutics* 187 (1999), pp. 259-272.

Norman Haber, "Electromolecular Propulsion (EMP): a Rapid, Simple Method for Analyzing Dyes Used in Microscopy," *Biotechnic & Histochemistry*, vol. 73, No. 2, Feb. 1998, pp. 59-69.

Norman Haber, "Chemoelectronic mobilization of chemical species in low-conductivity fluids: New electrokinetic effect," *Proc. Natl. Acad. Sci. USA*, Biochemistry, vol. 79, Jan. 1982, pp. 272-276.

Heller et al., "Membrane electrophoresis of DNA," *Electrophoresis* 1993, vol. 14, pp. 162-164.

\* cited by examiner

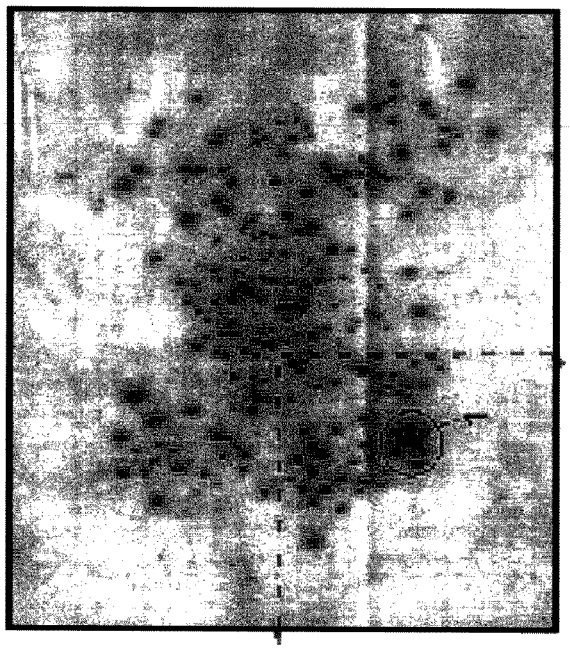
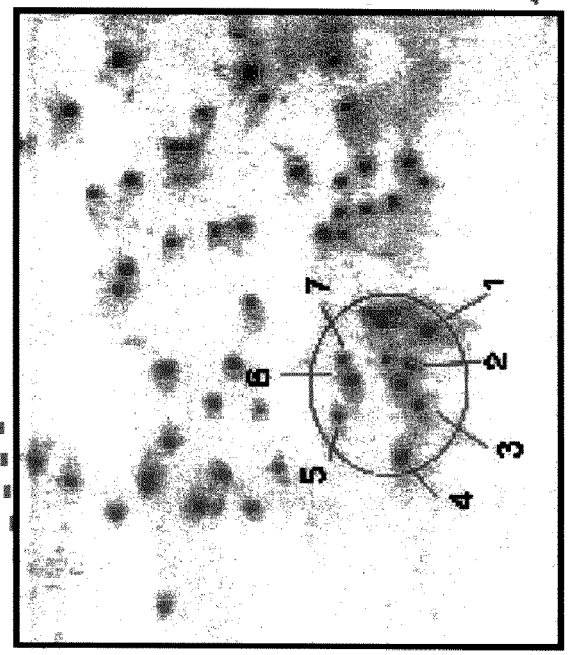
FIG. 6A
FIG. 6B

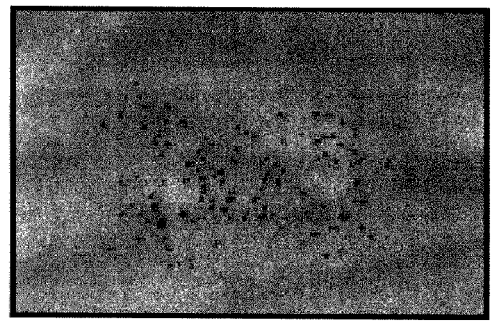
FIG. 9A
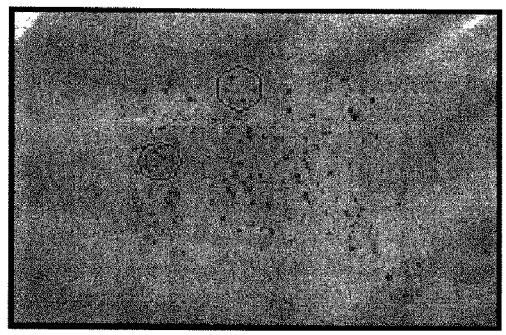 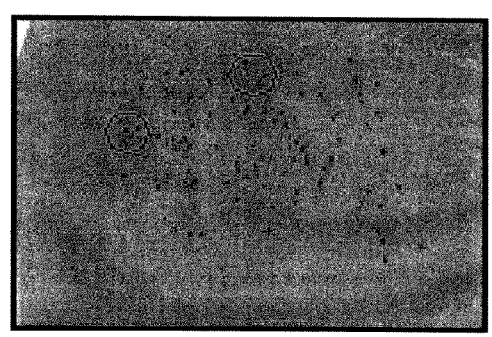
FIG. 9B            FIG. 9C
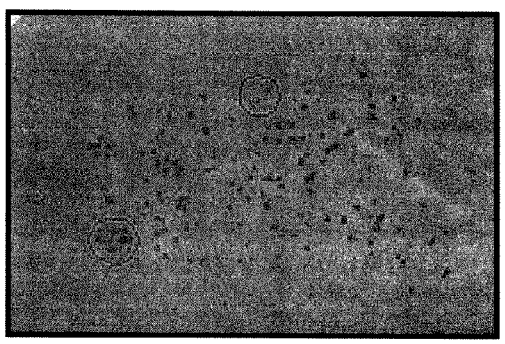 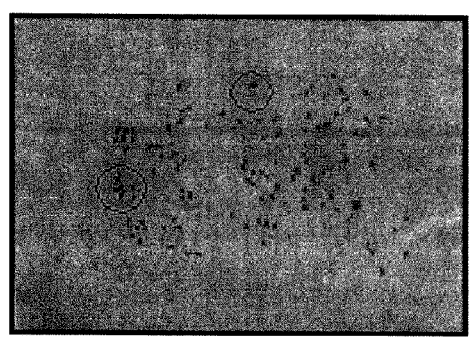
FIG. 9D            FIG. 9E

METHOD FOR DETECTING DISEASE MARKERS

CROSS-REFERENCE TO RELATED APPLICATION

This application claims the benefit of U.S. Provisional Application No. 60/962,081, filed Jul. 26, 2007, the entire disclosure of which is incorporated herein by reference.

FIELD OF THE INVENTION

This invention relates to the identification of specific disease markers, in particular the identification of markers specific for a given cancer or cancer stage, and the use of such markers to determine a diagnosis or prognosis for a subject.

BACKGROUND OF THE INVENTION

Cancer is the second leading cause of human mortality. In the United States alone, cancer causes the death of well over a half-million people annually, with some 1.4 million new cases diagnosed per year. Carcinomas of the breast, prostate, lung, colon, pancreas, and ovary are particularly lethal, because of the propensity of these cancers to produce fatal metastases. Even those cancer patients who initially survive their primary cancers can suffer physical and psychological debilitation following treatment, and many experience a recurrence of the disease.

Cancer morbidity and mortality can, however, be greatly reduced by early diagnosis and treatment. Thus, an intensive worldwide effort had been aimed at identifying truly specific, early-stage diagnostic and prognostic markers for cancers. Research efforts in these areas have increased the availability of useful molecular diagnostic and diagnostic imaging technologies, but progress in this area has been slow and generally uneven.

For example, alleles of the BRCA1 and BRCA2 genes have been linked to hereditary and early-onset breast cancer (Wooster, et al., Science, 265: 2088-2090 (1994)). Detection of mutated BRCA1 and BRCA2 alleles or their gene products has therefore been proposed as a means for detecting breast cancer (Miki, et al., supra). However, the BRCA1 and 2 genes are of limited use as a cancer markers, because mutations in these genes fail to account for the majority of breast cancers (Ford, et al., British J. Cancer, 72: 805-812 (1995)). Moreover, breast cancer has been generally classified into four different stages (I-IV), with Stage I being early cancerous and Stage IV being metastatic. Markers specific for each stage have yet to be identified.

SELDI-TOF mass spectrometry has been used for detecting putative breast cancer markers from serum, nipple aspirate fluid and others but the results were both confusing and contradictory. For example, markers reported by Laronga et al (Dis. Markers 19: 229-38 (2003)) was later found by Gast et al to be unreliable (Cancer Biomarkers 2: 235-48 (2006)). Gene profiling has been suggested as an alternative to the unreliable SELDI method. Several gene profiling kits such as MammaPrint and OncotypeDX are available for detecting breast cancer. They are based on the principle that when genes are damaged (as in the case of breast cancer), they will turn on some other genes that should normally be off and silence others that should be on. The premise is that the pattern of genes turned on in diseased tissue is abnormal, and can be used to predict disease progression, long-term survival, and how well patients will respond to drugs and radiation. Predictions based on gene profiles are not accurate and sometimes wrong.

Another cancer with a relatively high incidence and poor prognosis is pancreatic adenocarcinoma (PA). The molecular basis underlying the pathogenesis of PA is unknown, and the ability to detect early lesions for resection remains a challenge despite advances in diagnostic imaging methods. Furthermore, distinguishing PA from benign pancreatic diseases, especially chronic pancreatitis, is difficult because of the similarities in radiological and imaging features and the lack of clinical symptoms specific for PA.

Serologic assays for breast cancer and PA are easily performed, inexpensive, analytically-sensitive and can be serially performed over time with relative ease. To date, however, there exists no serologic assay which can specifically and reliably detect these or other cancers.

For example, several non-specific breast cancer markers, including glycosyl transferases (Ip et al., Cancer Res., 38: 723-728 (1978); Dao et al., J. Natl. Cancer Inst., 65: 529-534 (1980)) and glycolipids (Kloppel et al., Proc. Natl. Acad. Sci. USA, 74: 3011-3013 (1977)) can be detected by serologic assays. Serum-based immunoassays can also detect circulating human mammary epithelial antigens which may be present in elevated amounts in the plasma of breast cancer patients (Ceriani et al., Proc. Natl. Acad. Sci. USA, 79: 5420-5424 (1982); Hayes, J. Clin. Invest., 75: 1671-1678 (1985)). However, detection of these markers and antigens is not a widely accepted clinical assay for breast cancer.

Serum-based immunoassays have been used to detect blood group-related antigens and glycoprotein markers commonly used as clinical tumor markers for PA, such as CA19-9, CA72-4, CA125, and more recently CA242. However, there are contradictory reports about the specificity and sensitivity of these immunoassays. For example, the specificity of the CA19-9 serum assay for detecting PA ranged from 69% to 93%, and the sensitivity varied between 46% and 98% (Eskelinen et al, Scand. J. Gastroenterol. 34: 833-844 (1999)). CA19-9 antigen also exhibited elevated serum levels in some benign pancreatic diseases (Slesak et al., Cancer 89: 83-88 (2000)).

Furthermore, in many serologic assays, the presence of cancer markers can be obscured by major serum proteins such as serum protein (which constitutes approximately 50% of serum proteins), immunoglobulin G (IgG), heptoglobin, and alpha-1-antitrypsin.

Conventional two-dimensional polyacrylamide gel electrophoresis ("2-D PAGE"), first developed by O'Farrell (J. Biol. Chem. 250: 4007-4021, 1975), is a common serologic assay used to detect cancer markers. In this method, proteins are first separated under denaturing conditions according to their isoelectric points, followed by separating the proteins according to their molecular weights in a second dimension in the presence of an ionic detergent.

In order to carry out biological functions, proteins usually form complexes with other proteins. On average, a protein forms complexes with 4 or 5 different partners. Understanding protein-protein interaction is therefore the key to unlock the mystery of cell function, and how diseases occur and progress. The commonly used 2-D polyacrylamide gel electrophoresis system (2-D PAGE) cannot separate protein complexes because it is carried out under denaturing conditions which destroys all protein complexes.

Conventional 2-D PAGE has other disadvantages. The separation of serum proteins on the gel involves multiple steps, and generally takes one to two days to complete. The proteins must then be "blotted," or transferred onto high protein binding capacity, low porosity polymer membranes so they can be detected by staining, immunodetection (e.g., Western blot), mass spectrometry, amino acid sequence analysis or the like. The blotting step is also time consuming, and can result in loss of separated protein due to inefficient transfer out of the gel. For example, the retention of low molecular weight proteins by nitrocellulose is influenced by the presence of methanol in the transfer buffer (Pluskal et al., Biotechniques 4: 272-283, 1986). Higher molecular weight proteins are also known to have lower transfer efficiency onto blotting membranes. Detection of small amounts of separated proteins can therefore be difficult. And as indicated above, any protein-protein interactions or biological activities of the separated proteins are not preserved under the denaturing conditions used in conventional 2-D PAGE techniques.

Conventional 2-D PAGE also typically employs aqueous buffers, because such buffers provide the high conductivity needed for protein separation. However, the use of aqueous buffers can generate excessive heat during electrophoresis, which can damage the protein sample or electrophoretic equipment. The use of aqueous buffers also prevents the efficient separation of hydrophobic proteins.

On average, a protein forms complexes with 4 or 5 different partners. The commonly used 2-D polyacrylamide gel electrophoresis system (2-D PAGE) cannot separate protein complexes from one another while maintaining the integrity of the complexes because 2-D PAGE is carried out under denaturing conditions which destroys all protein complexes. An electrophoretic system that is fast, requiring very small amount of serum sample and also allows the separation of both proteins and protein complexes, while maintaining the integrity of the latter, would be desirable for detecting cancer and other disease marker proteins.

A one dimensional electro-separation method has been developed which uses water-miscible organic solvents to separate small molecules on separation substrates such as filter paper (see U.S. Pat. No. 4,146,454; Haber N., PNAS USA, 79:272-276, 1982; and Haber N., *Biotechnic & Histochemistry,* 73: 59-70, 1998). In this method, which is called "electro-molecular propulsion" or "EMP," an electronic charge is imposed on the molecules by an unknown mechanism, which causes the molecules migrate within an applied electrical field. EMP is therefore different from conventional electrophoresis systems, in which movement of molecules in an electric field depends on ionic species dissolved in an electrolytically conductive medium. See Haber N., *Biotechnic & Histochemistry,* 1998, supra.

The EMP technique does not appear suitable for analysis of ampholytic biopolymers such as proteins, primarily because the substrates used in the EMP process do not bind proteins well, and proteins separated by EMP begin to diffuse on the substrates almost immediately after cessation of the electric current. This diffusion of proteins has greatly limited the usefulness of the EMP process, and no 2-D protein separation procedure employing this technique has been reported.

Therefore, even with advances in molecular diagnostic and diagnostic imaging techniques, a simple and effective assay for breast cancer and PA (and indeed other cancers) remains lacking. What is needed, therefore, is a method for rapidly detecting cancer and other disease marker proteins present in serum or other bodily fluids, for example by electrophoretic separation. The electrophoretic method should employ low conductivity, organic solvent buffers compatible with hydrophilic, hydrophobic and low molecular weight proteins. The buffers should also have low conductivity so as to minimize heat generation during electrophoretic separation, and are preferably non-denaturing to preserve protein binding interactions and biological activities. Ideally, the electrophoretic separation substrate should minimize diffusion of the separated molecules after electrophoresis is completed, and eliminate the need for transferring the separated molecules from the separation matrix onto a blotting membrane.

SUMMARY OF THE INVENTION

It has now been found that markers indicating a certain disease, in particular cancer markers, can be detected by electrophoretically separating proteins and protein complexes by membrane electrophoresis. As used herein, "membrane electrophoresis" refers to the electrophoresis of biological samples on polymeric protein binding membranes, as described more fully below. Membrane electrophoresis is carried out on the surface of a polymeric protein binding membrane, as opposed to other types of electrophoresis which are carried out on paper or through polyacrylamide gels. Unless indicated to the contrary, the term "protein" includes both proteins and protein complexes. Thus, a sample "comprising proteins" means a sample that contains proteins, protein complexes, or both, and the expression "separating the proteins" with respect to an electrophoretic separation carried out on such a sample includes the separation of proteins, protein complexes, or both. The electrophoretic separation is carried out in a low conductivity, water-miscible organic solvent buffer. As the buffer is not aqueous-based, both hydrophobic and small molecular weight proteins can be readily separated. The low conductivity of the organic solvent buffer also minimizes heat generation during electrophoretic separation. Consequently, enough voltage can be applied to the electrophoresis system that separation of molecules is effected in only a fraction of the time required for traditional aqueous electrophoresis systems. Moreover, as protein separation is carried out directly on the blotting membrane, there is no need for the subsequent transfer of separated proteins, as required in the Western blotting step.

The invention therefore provides a method of identifying disease-specific markers in a test subject, comprising the following steps. A sample of biological fluid comprising proteins is obtained from at least one normal subject, and the proteins in the biological sample are separated by membrane electrophoresis to obtain a normal separation profile. A sample of biological fluid comprising proteins is also obtained from at least one diseased subject, and the proteins in the biological sample are separated by membrane electrophoresis to obtain a disease separation profile. The normal separation profile on the membrane is compared to the disease separation profile on the membrane to determine the difference in the number and distribution of proteins between the normal and disease separation profiles. The difference in the number and distribution of proteins between the normal and disease separation profiles represents the disease-specific markers. The phrase "separation profile" as used herein means a separation profile on a membrane after membrane electrophoresis.

The invention also provides method of diagnosing a disease in a test subject, comprising the following steps. A sample of biological fluid comprising proteins is obtained from the test subject, and the proteins in the biological sample are separated by membrane electrophoresis to obtain a test separation profile. A standard separation profile is provided, and the test protein separation profile is compared to the standard separation profile. A substantial similarity between the test separation profile and the standard separation profile indicates that the test subject has the disease represented by the standard separation profile.

The invention further provides a method of staging cancer in a test subject, comprising the following steps. A sample of biological fluid comprising proteins is obtained from the test subject, and the proteins in the biological sample are separated by membrane electrophoresis to obtain a test separation profile. The test separation profile is then compared to a set of standard separation profiles which comprise a plurality of stage-specific separation profiles. A substantial similarity of the test separation profile to a stage-specific separation profile indicates that the test subject has cancer of the stage represented by that stage-specific separation profile.

The invention further provides a method of staging breast cancer in a test subject, comprising the following steps. A sample of biological fluid comprising proteins is obtained from the test subject, and the proteins in the biological sample are separated by membrane electrophoresis to obtain a test separation profile. The test separation profile is compared to a set of standard separation profiles which comprise a first, second, third and fourth stage-specific separation profile representing, respectively, stage I, II, III or IV of breast cancer. A substantial similarity of the test separation profile to a breast cancer stage-specific separation profile indicates that the subject has breast cancer of the stage represented by that stage-specific separation profile.

The invention still further provides a method of determining the prognosis of a subject with cancer, in particular breast cancer, by staging the cancer in the subject.

BRIEF DESCRIPTION OF THE FIGURES

FIGS. 6A and 6B represent two-dimensional membrane electrophoretic separation profiles of pancreatic cancer serum markers. In FIG. 6A, a serum sample from a subject with pancreatic cancer was fractionated and an aliquot of the hydrophobic fraction was loaded at the center of the membrane and subjected to two-dimensional membrane electrophoresis. In FIG. 6B, an aliquot of the same hydrophobic fraction used for FIG. 6A was loaded in the upper right quadrant of a membrane, instead of the center of the membrane, and subjected to two-dimensional membrane electrophoresis to try and better resolve the cluster of proteins encircled in FIG. 6A. The dashed marks connecting FIG. 6A to FIG. 6B indicate analogous regions of protein spots of the two figures. The encircled areas indicate analogous clusters of protein spots. The seven spots labeled in FIG. 6B indicate spots which were cut from the PVDF membrane, eluted, and subjected to mass spectrometry.

FIGS. 9A to 9E represent two-dimensional membrane electrophoretic separation profiles of hydrophobic fractions of serum derived from: a normal subject (FIG. 9A), or subject with Stage I breast cancer (FIG. 9B), Stage II breast cancer (FIG. 9C), Stage III breast cancer (FIG. 9D) and Stage IV breast cancer (FIG. 9E). Encircled areas indicate regions of protein marker changes.

DETAILED DESCRIPTION OF THE INVENTION

Figure 1:
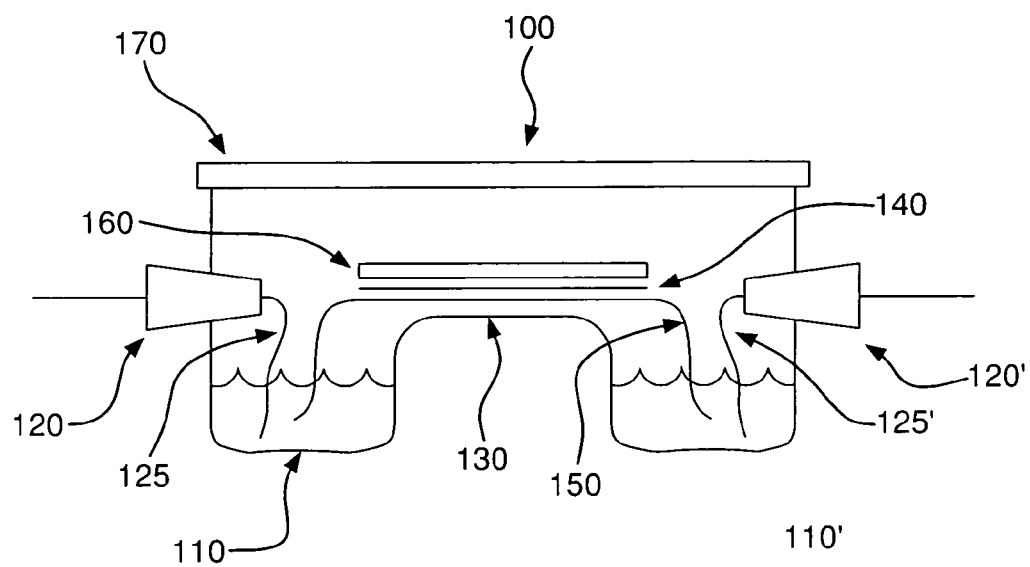
FIG. 1 is a side cutaway view of a horizontal electrophoresis unit of the invention.

All percentages referred to herein are by volume, unless otherwise indicated.

Membrane electrophoresis allows the rapid, high resolution separation of proteins and protein complexes directly on polymeric membranes. Membrane electrophoresis is carried out on a membrane, in contrast to conventional electrophoresis which is carried out on a polyacrylamide gel. Membrane electrophoresis is conducted in low conductivity, water-miscible organic solvent buffers. The low conductivity of the organic solvent buffer minimizes heat generation, and the water-miscible nature of the organic solvent buffer permits the analysis of hydrophobic and low molecular weight proteins as well as hydrophilic proteins. Membrane electrophoresis, when conducted under non-denaturing conditions, allows the detection of enzymatic activities, protein-protein interactions and protein-ligand interactions in the separated proteins.

As used herein, "protein" refers to a molecule comprising at least two amino acid residues covalently linked by peptide bonds or modified peptide bonds (e.g., peptide isosteres). No limitation is placed on the maximum number of amino acids which may comprise a protein. The amino acids comprising the proteins referred to herein are understood to be either D- or L-amino acids, with L-amino acids being preferred. In addition, the component amino acids may be β-amino acids, or custom synthesized amino acids or peptidomimetic fragments; e.g. a Friedinger γ lactam, a peptoid or the like, or mixtures of any of these substances.

The proteins referred to herein can also be associated with one or more other molecules, including one or more other proteins (i.e., as a protein complex), or with one or more metal atoms or metal complexes such as, for example a zinc finger protein. For example, a protein may comprise a homo- or heteromultimeric protein, an antibody/antigen complex, or a ligand/receptor complex. As used herein, the association of a protein with another protein or non-protein molecule is termed a "protein-binding interaction." The proteins referred to herein may also exhibit biological activities; e.g., enzymatic activities.

The proteins referred to herein can also contain modifications. Such modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA-mediated addition of amino acids to proteins such as arginylation, and ubiquitination. See, for example, *Proteins—Structure and Molecular Properties*, 2nd Ed., T. E. Creighton, W. H. Freeman and Company, New York, 1993; Wold F, Posttranslational Protein Modifications: Perspectives and Prospects, pgs. 1-12 in *Posttranslational Covalent Modification of Proteins*, B. C. Johnson, Ed., Academic Press, New York, 1983; Seifter et al., "Analysis for protein modifications and nonprotein cofactors," *Meth. Enzymol.* (1990) 182: 626-646; and Rattan et al. (1992), "Protein Synthesis: Posttranslational Modifications and Aging," *Ann NY Acad Sci* 663: 48-62, the entire disclosures of which are herein incorporated by reference.

Membrane electrophoresis can detect disease-specific protein markers which are typically represented as only a small fraction of the proteins in a biological sample. In the practice of the invention, biological samples comprising proteins are obtained from normal and diseased subjects, and are subjected to membrane electrophoresis to create normal and disease separation profiles. The normal and disease separation profiles are then compared. The differences between the number and/or distribution of protein spots on the disease separation profile as compared to the normal separation profile represent the disease-specific markers.

As used herein, a "diseased subject" is a subject who has a disease; i.e., any abnormal condition of the body or mind that causes discomfort or dysfunction in that subject. As used herein, a "normal" subject is a subject who does not have a disease, or does not have the same disease as the diseased subject.

A biological sample comprises any type of biological material comprising proteins that can be subjected to membrane electrophoresis for detection of disease-specific markers. For example, biological samples can be derived from animals, such as birds, fish, reptiles, and mammals. Preferably, biological samples are derived from mammals, especially canines, felines, rodents (e.g., mice and rats), bovines, ovines, porcines and primates (e.g., humans). In a particularly preferred embodiment, the biological samples are derived from humans. As used herein, "derived from" with respect to a biological sample includes material obtained directly from a subject (e.g., bodily fluid or biopsy material), or cells or tissue which have been maintained ex vivo for any length of time, such as cell, tissue and organ cultures. The biological sample can be separated into hydrophobic or hydrophilic fractions, according to techniques within the skill in the art, and these fractions can be subjected to membrane electrophoresis. Thus, as used herein, "biological sample" includes samples fractionated into hydrophobic or hydrophilic fractions, as well as unfractionated samples.

In a preferred embodiment, the biological sample comprises a bodily fluid, including blood, serum, plasma, lymph, saliva, mucus, sputum, pus, perspiration, urine, stool, gastrointestinal secretions, cochlear fluid, synovial fluid, cerebrospinal fluid, lachrymal fluid, vitreous humor, semen, vaginal secretions, and mammary gland secretions. In a particularly preferred embodiment, the biological sample comprises blood, serum or plasma. In this preferred embodiment, the blood serum or plasma can be unfractionated, or can be fractionated into hydrophilic and hydrophobic fractions according to techniques within the skill in the art.

A separation profile is created by subjecting a biological sample to membrane electrophoresis, so the proteins comprising the biological sample are separated and can be visualized. Membrane electrophoresis, and techniques for visualizing proteins separated by membrane electrophoresis, are described in more detail below. A separation profile can comprise proteins from a single biological sample which have been separated on a single protein-binding membrane, or can comprise proteins from multiple biological samples which have been separated on a single protein-binding membrane. A separation profile can also comprise proteins from a single biological sample which have been separated on a plurality of individual protein-binding membranes; i.e., as multiple replicates.

A "normal separation profile" is created by subjecting one or more biological samples from a normal subject to membrane electrophoresis. A "disease separation profile" is created by subjecting one or more biological samples from a subject who has been diagnosed with a disease to membrane electrophoresis. In the practice of the present methods, at least one normal and at least one disease separation profile are created under the same conditions; that is, similar amounts of biological samples from normal and diseased individuals are subjected to membrane electrophoresis using the same buffers, voltage, separation time, etc. Such normal and disease separation profiles can then be validly compared to detect the disease specific markers.

If desired, the proteins from the disease separation profile which comprise the disease-specific markers can be isolated from the protein binding membrane and identified. Alternatively, the proteins from the disease separation profile which comprise the disease-specific markers can be identified without removing the proteins from the membrane (for example by immunodetection).

Diseases for which disease-specific markers can be detected by the present methods include cancer. For example, membrane electrophoresis can be used to detect disease-specific markers for cancers of at least the following histologic subtypes: sarcoma (cancers of the connective and other tissue of mesodermal origin); melanoma (cancers deriving from pigmented melanocytes); carcinoma (cancers of epithelial origin); adenocarcinoma (cancers of glandular epithelial origin); cancers of neural origin (glioma/glioblastoma and astrocytoma); and hematological neoplasias, such as leukemias and lymphomas (e.g., acute lymphoblastic leukemia, chronic lymphocytic leukemia, and chronic myelocytic leukemia).

Membrane electrophoresis can also be used to detect disease-specific markers for cancers having their origin in at least the following organs or tissues, regardless of histologic subtype: breast; tissues of the male and female urogenital system (e.g. ureter, bladder, prostate, testis, ovary, cervix, uterus, vagina); lung; tissues of the gastrointestinal system (e.g., stomach, large and small intestine, colon, rectum); exocrine glands such as the pancreas and adrenals; tissues of the mouth and esophagus; brain and spinal cord; kidney (renal); pancreas; hepatobiliary system (e.g., liver, gall bladder); lymphatic system; smooth and striated muscle; bone and bone marrow; skin; and tissues of the eye.

Membrane electrophoresis can also be used to detect disease-specific markers for cancers or tumors in any prognostic stage of development, as measured, for example, by the "Overall Stage Groupings" (also called "Roman Numeral") or the Tumor, Nodes, and Metastases (TNM) staging systems. Appropriate prognostic staging systems and stage descriptions for a given cancer are known in the art, for example as described in the National Cancer Institute's "CancerNet" Internet website.

Membrane electrophoresis can further be used to detect disease-specific markers for bacterial infections, (e.g., anthrax, Lyme disease, Legionnaire's disease, meningitis, whooping cough, typhoid, dysentery, pneumonia, bubonic and pneumonic plague, cholera, typhus, tuberculosis, diphtheria, polio and Staphylococcus infections); viral infections (e.g., HIV/AIDS, herpes, smallpox, chickenpox, hepatitis, influenza, mumps, measles, rubella); disorders or conditions of the immune system (e.g., allergic response, inflammation, systemic lupus erythematosus, Goodpasture disease); metabolic disorders (e.g., phenylketonuria, non-insulin dependent diabetes); and neurologic disorders (e.g., Alzheimer's disease, Parkinson's disease, Kreutzfield-Jakob syndrome, migraine headaches), and other diseases.

Once a disease separation profile with disease specific markers has been identified, that disease separation profile can be used as a standard against which a test separation profiles can be compared. As used herein, a disease separation profile in which disease specific markers have been identified is called a "standard separation profile."

Thus, the invention also provides a method of diagnosing a disease in a test subject, in which a biological sample comprising proteins is obtained from the test subject. The proteins in the biological sample are separated by membrane electrophoresis to obtain a test separation profile, which is then compared to a standard separation profile. As stated above, a substantial similarity between the test separation profile and the standard separation profile indicates that the subject has the disease represented by the standard separation profile.

For the purposes of the present invention, a standard separation profile "represents" the disease suffered by the subject who provided the biological sample(s) used to produce standard separation profile. For example, if a standard separation profile is produced from samples obtained from a subject who has pancreatic cancer, then that standard separation profile "represents" pancreatic cancer.

In the practice of the present methods, a "test separation profile" is a separation profile obtained by subjecting one or more biological samples obtained from a test subject to membrane electrophoresis.

As used herein, a "test subject" is any subject who is at risk for, or who is suspected of having, a disease. Test subjects can be readily identified by an ordinarily skilled physician, by the identification of well-known risk factors or symptoms of a given disease.

As used herein, a test separation profile is "substantially similar" to a standard separation profile when both separation profiles exhibit the same protein separation pattern (including the number, placement and/or relative intensity of protein spots), within the normal variations expected in 1) intensity of protein spots, 2) the absolute distance of each protein spot from the origin along the length and/or width of the membrane and 3) the relative distance of each protein spot from other protein spots on the membrane. One skilled in the art is familiar with, and can readily determine, the magnitude of these expected variations.

It is understood that a "protein spot" on a protein binding membrane can comprise a single protein, a protein complex, or a plurality of proteins. A protein spot can be visualized by any suitable visualization technique, as described in more detail below.

In one embodiment, the present invention provides a method of staging cancer in a subject, using membrane electrophoresis to create test and standard separation profiles.

The staging of cancer refers to the grouping of subjects according to the extent of their disease. As used herein, a cancer "stage" is a defined point in the progression of a given cancer, which conveys certain information to the physician regarding disease penetration and prognosis. Generally, subjects who have a more advanced stage of cancer have a poorer prognosis than subjects with cancer in the earlier stages. Thus, the invention also provides a method of determining the prognosis of a test subject with cancer, by staging the cancer in the subject as described below.

Well-known cancer staging systems include the "Overall Stage Groupings" (also called "Roman Numeral") or the Tumor, Nodes, and Metastases (TNM) staging systems mentioned above, which are based on clinical observation of the subject (both externally and by surgery), and on histological examination of cancerous tissue after surgical resection. The stage of a cancer afflicting a subject can be identified using such staging systems. Once the cancer stage in a subject has been identified, one or more standard separation profiles which are representative of a given cancer stage (hereinafter called "stage-specific separation profiles") can be created by subjecting biological samples from such subjects to membrane electrophoresis.

A test subject having a cancer of unknown stage is identified using standard diagnostic criteria, for example as described in *Cancer: Principles and Practice of Oncology*, (3rd edit., DeVita V T, Hellman S, and Rosenberg S A, eds.), 1989, J. B. Lipincott Co., Phila., Pa., the entire disclosure of which is herein incorporated by reference. One or more biological samples comprising proteins (for example of a biological fluid or of tumor tissue) are obtained from the test subject, and the proteins in the biological sample are separated by membrane electrophoresis to obtain a test separation profile. The test separation profile is compared to stage-specific standard separation profiles to determine what cancer stage the test subject has reached. A substantial similarity of the test separation profile to a stage-specific separation profile indicates that the subject has cancer of the stage represented by that stage-specific separation profile.

For the purposes of the present invention, a stage-specific standard separation profile "represents" the stage of cancer suffered by the subject who provided the biological sample(s) used to produce stage-specific standard separation profile. For example, if a stage-specific standard separation profile is produced from samples obtained from a subject who has stage I breast cancer, then that standard separation profile "represents" stage I breast cancer.

In a preferred embodiment, the invention provides a method of staging breast cancer in a test subject, using membrane electrophoresis to create test and standard separation profiles. In the practice of this embodiment, a test subject with breast cancer is identified using standard criteria for diagnosing cancer. Such criteria are well-known in the art; for example, as described in Henderson I C et al., "Cancer of the Breast," pp. 1197-1268, in *Cancer: Principles and Practice of Oncology*, (3rd edit., DeVita V T, Hellman S, and Rosenberg S A, eds.), 1989, J. B. Lipincott Co., Phila., Pa., the entire disclosure of which is herein incorporated by reference.

One or more biological samples comprising proteins (for example of a biological fluid or of breast tumor tissue) are obtained from the test subject, and the proteins in the biological sample are separated by membrane electrophoresis to obtain a test separation profile. The test separation profile from the test subject is compared to stage-specific separation profiles representing, respectively, stage I, II, III or IV of breast cancer. A substantial similarity of the test separation profile to a breast cancer stage-specific separation profile indicates that the subject has breast cancer of the stage represented by that stage-specific separation profile.

Stage-specific separation profiles representing breast cancer stages I, II, III or IV are prepared from biological samples obtained from subjects with breast cancer of a known stage, by subjecting such biological samples to membrane electrophoresis. The ordinarily skilled physician can readily identify subjects with breast cancer of a known stage, for example by evaluating subjects according to the TNM staging system adopted by the International Union against Cancer (UICC) and the American Joint Commission on Cancer Staging and End Results Reporting (AJC) in 1983. This staging system is described below.

| Stage I | T1a or T1b, | N0 or N1a, | M0 |
|---|---|---|---|
| Stage II | T0, | N1b, | M0 |
| | T1a or T1b, | N1b | M0 |
| | T2a or T2b, | N0, N1a, or N1b | M0 |
| Stage III | T1a or T1b, | N2 | M0 |
| | T2a or T2b, | N2 | M0 |
| | T3a or T3b, | N0, N1 or N2, | M0 |
| Stage IV | T4 | any N, | any M |
| | any T, | N3, | any M |
| | any T, | any N, | M1 | wherein:
| | |
|---|---|
| T | Primary tumors |
| T1 | Tumor 2 cm or less in its greatest dimension |
| | a. No fixation to underlying pectoral fascia or muscle |
| | b. Fixation to underlying pectoral fascia or muscle |
| T2 | Tumor more than 2 cm but not more than 5 cm in its greatest dimension |
| T3 | Tumor more than 5 cm in its greatest dimension |
| | a. No fixation to underlying pectoral fascia or muscle |
| | b. Fixation to underlying pectoral fascia or muscle |
| T4 | Tumor of any size with direct extension to chest wall or skin. Note: Chest wall includes ribs, intercostals muscles, and serratus anterior muscle, but not pectoral muscle |
| | a. Fixation to chest wall |
| | b. Edema (including peau d'orange), ulceration of the skin of the breast, or satellite skin nodules confined to the same breast |
| | c. Both of the above |
| | d. Inflammatory carcinoma |
| (Dimpling of the skin, nipple retraction, or any other skin changes except those in T4b may occur in T1, T2, or T3 without affecting the classification.) | |
| N | Regional lymph nodes |
| N0 | No palpable homolateral axillary nodes |
| N1 | Movable homolateral axillary nodes |
| | a. Nodes not considered to contain growth |
| | b. Nodes considered to contain growth |
| N2 | Homolateral axillary nodes containing growth and fixed to one another or to other structures |
| N3 | Homolateral supraclavicular or infraclavicular nodes containing growth or edema of the arm. |
| M | Distant metastasis |
| M0 | No evidence of distant metastasis |
| M1 | Distant metastasis present, including skin involvement beyond the breast area |

Information regarding the stage of breast cancer in a subject can be used in determining the prognosis of subjects with breast cancer, as is within the skill in the art. For example, the prognosis of subjects with breast cancer decreases with the increasing breast cancer stage. Thus, the invention also provides a method of determining the prognosis of a test subject with breast cancer, by staging breast cancer in the subject as described above.

As discussed above, separation profiles are obtained by subjecting biological samples to membrane electrophoresis. Membrane electrophoresis is described below. Membrane electrophoresis was also described in commonly owned International patent application publication no. WO 2004/025250, filed Sep. 9, 2003, published on Mar. 25, 2004; and in commonly owned United States Patent Application publication no. 2004/0121488, published on Jun. 24, 2004. The entire disclosures of the aforesaid patent publications are incorporated herein by reference.

The electrophoresis buffers for use in membrane electrophoresis comprise water-miscible organic solvents which have been formulated to exhibit low conductivity. The use of water-miscible organic solvent buffers under non-denaturing conditions allows for the separation of both hydrophilic and hydrophobic protein complexes. As used herein, an organic solvent buffer has "low conductivity" when the buffer produces a current of about 0.0001 mA/cm$^2$ membrane to about 0.2 mA/cm$^2$ membrane when subjected to a fixed voltage (e.g., 3.5 kV) One of ordinary skill in the art can readily determine the conductivity of an organic solvent buffer using techniques known in the art. A convenient technique for measuring conductivity of buffers for use in the present invention is to electrophorese a protein sample on a 1 cm by 8 cm membrane at 3.5 kV, as described in Example 2 below.

The present low conductivity organic solvent buffers comprise one or more high boiling point organic solvents that exhibit little to no conductivity. Such solvents are referred to as the "base" solvents, and are present in the buffer in a final concentration of about 1% to about 80%, preferably of about 20% to 50%, for example about 40%. Suitable organic solvents for use as base solvents include, for example, propylene carbonate (also known as 1,2-propanediol cyclic carbonate) (bp=240° C.); ethylene cyclic carbonate (bp=245° C.); dimethyl phthalate (bp=282° C.); diethyl phthalate (bp=294° C.); ethylene glycol (bp=195° C.); propylene glycol (bp=185° C.); butylene glycol (bp=180° C.); dimethyl sulfoxide (bp=189° C.); methyl carbitol (bp=193° C.); and mixtures thereof. Preferred base solvents are propylene carbonate, ethylene cyclic carbonate or mixtures thereof.

Proteins are known to tightly bind to the membranes used in membrane electrophoresis (see below). In order to generate sufficient current to cause migration of proteins on the membrane, one or more conductivity enhancers are added to the base solvent.

As used herein, a "conductivity enhancer" is an organic solvent or other substance that causes an increase in current when added to a base solvent, as measured at a fixed voltage (e.g., 3.5 kV) using prewetted 1 cm by 8 cm PVDF membrane strips of about 0.1 to about 0.15 mm thickness. The final concentration of each conductivity enhancer in the low conductivity organic solvent buffer is preferably about 0.1% to about 50%, more preferably about 5% to about 30%. Suitable conductivity enhancers include: amide compounds such as formamide, acetamide, propionamide, butyramide, toluamide, benzamide, lactamide, nicotinamide, and mixtures thereof; amide derivatives such as N-methyl formamide, N-methyl acetamide, N-methyl propionamide, and N-methyl butyramide; 2-furaldehyde; furfuryl alcohol; tetrahydrofurfuryl alcohol; salicylaldehyde; guaiacol; phenol; boric acid; fumaric acid; piperazine; and mixtures thereof. Preferred low conductivity organic solvent buffers comprise at least two conductivity enhancers. For example, the low conductivity organic solvent buffer can comprise, in addition to the base solvent, salicylaldehyde and furfuryl alcohol; a mixture of formamide, 2-furaldehyde and benzamide; a mixture of formamide and furfuryl alcohol; a mixture of formamide and tetrahydrofurfuryl alcohol or a mixture of formamide, 2-furaldehyde and boric acid.

The conductivity enhancers can, however, cause the organic solvent buffer to produce high current and excessive heat during electrophoresis. In general, heat will be generated during electrophoresis with the present buffers when the current is above 1.5 mA. Addition of one or more conductivity suppressors (also called "heat suppressors") to the base solvent/conductivity enhancer mixture can reduce heat production during electrophoresis with only a minimal effect on the migration of proteins on the membrane. Thus, the present organic solvent buffers preferably contain one or more conductivity suppressors.

As used herein, "excessive heat production" includes the generation of sufficient heat to: denature or alter the proteins being separated; boil the electrophoresis buffer or cause the buffer to entirely evaporate from the membrane; melt, char or otherwise damage the membrane or electrophoresis apparatus; or otherwise interfere with the electrophoretic separation.

As used herein, a "conductivity suppressor" is an organic solvent or other substance that causes a decrease in current when added to a base solvent which contains at least one conductivity enhancer, as measured at a fixed voltage (e.g. 3.5 kV) using prewetted 1 cm by 8 cm PVDF strips of about 0.15 mm thickness (see Examples 1 and 2, below). The final concentration of each conductivity suppressor in the low conductivity organic solvent buffer, when present, is preferably about 0.1% to about 50%, more preferably about 5% to about 30%. Suitable conductivity suppressors include: dimethyl derivatives of formamide and acetamide; 1,3-butanediol; N-methyl pyrrolidinone; sorbitol; glycerol; caprolactone; methoxyethanol; and mixtures thereof. Preferred conductivity suppressors are a mixture of 1,3-butanediol, dimethyl formamide and dimethyl acetamide; or a mixture of 1,3-butanediol and N-methyl pyrrolidinone. A particularly preferred conductivity suppressor is 1,3-butanediol.

As discussed above, too high a concentration of conductivity enhancers in the organic solvent buffer can lead to high current and excessive heat generation during electrophoresis. It is also apparent that too high a concentration of conductivity suppressors in the organic solvent buffer can lead to inadequate protein migration rates. The concentration of conductivity enhancers and conductivity suppressors in the present low conductivity organic solvent buffers must therefore be balanced, so that the overall buffer conductivity remains low, yet adequate migration of proteins is achieved without excessive heat generation. One skilled in the art can readily determine the appropriate balance of conductivity enhancers and suppressors in the present organic solvent buffers.

A convenient method for producing a low conductivity organic solvent buffer of the present invention comprises the addition of at least one conductivity enhancer to a base solvent in measured amounts, until the solution is capable of generating a current, for example, about 0.025 mA/cm$^2$ membrane (0.15 mm thickness) during electrophoresis. If high current and excessive heat production is observed, one or more conductivity suppressors are added in measured amounts until heat generation is reduced to within acceptable limits. Exemplary low conductivity organic solvent buffers produced by this method are given as "Buffers A-B" in General Materials and Methods, below.

The pH of the low conductivity organic solvent buffers can be adjusted as desired, within the limits compatible with the particular buffer components. For example, the pH can be adjusted to a range of about pH 3 to about pH 10. It is understood, however, that low conductivity organic solvent buffers according to the present invention can have a pH outside of this range.

In one embodiment, organic solvent buffers of identical composition can be adjusted to different pH's. For example, a first amount of Buffer A of Example 1 can be adjusted to pH 4.5, and a second amount of Buffer A can be adjusted to pH 8.5. These first and second amounts of Buffer A can then be used sequentially in the two dimensional electrophoresis of proteins, for example as described below.

The separation substrate used in the present invention comprises a polymeric membrane. This membrane separation substrate is analogous to the gel matrix in conventional electrophoretic methods.

Membranes for use in the present invention must be compatible with the low conductivity organic solvent buffers discussed above. For example, cellulose-derived membranes (e.g., nitrocellulose, cellulose acetate or DEAE cellulose) are destroyed by the organic solvent buffers soon after contact, rendering them useless for membrane electrophoresis. Most other types of commercially available polymeric membranes are not damaged by the present organic solvent buffers.

Membranes for use in the present invention must also have a high protein binding capacity. As used herein, a "high protein binding capacity" means the membranes bind, at room temperature, at least about 20 μg protein/cm$^2$. Preferably, the membranes of the invention bind, at room temperature, at least about 50 μg protein/cm$^2$, and more preferably at least about 100 μg protein/cm$^2$ to about 400 μg protein/cm$^2$, for example about 150 μg protein/cm$^2$ or about 250 μg protein/cm$^2$.

Membranes for use in the present invention can be either hydrophobic or hydrophilic, and preferably have a low charge or a net neutral charge. For purposes of the present invention, it is understood that polymeric membranes designated as "neutral" are generally not devoid of charge, but either have a net neutral charge or a slight positive or negative charge. Without wishing to be bound by any theory, it is believed that proteins bind to hydrophobic polymeric membranes via hydrophobic interactions, and bind to hydrophilic membranes via ionic interactions.

Hydrophobic membranes suitable for use in the present invention include membranes comprising fluorinated polymers such as polyvinylidene difluoride (PVDF, also known in the art as polyvinylidene fluoride), polytetrafluoroethylene (PTFE), and the like; polyolefins such as polyethylene, polypropylene, polymethylpentene and the like; polystyrene or substituted polystyrenes; polysulfones such as polyethersulfone and the like; polyesters such as polyethylene terephthalate; polybutylene terephthalate and the like; polyacrylates and polycarbonates; polyurethane and vinyl polymers such as polyvinyl chloride and polyacrylonitriles; and mixtures of the above-listed polymers. Additionally, the hydrophobic membranes can comprise copolymers; e.g., of butadiene and styrene; fluorinated ethylene-propylene copolymer; and the like. Preferably, the hydrophobic membranes comprise polymeric fluorocarbons such as polyvinylidene difluoride (PVDF).

The hydrophobic membranes can also comprise modified forms of the above polymers, such as are known in the art. For example, hydrophobic polymeric membranes can be modified to contain fixed formal positive charge groups by contacting the membranes with a polyamine or a polyamidopolyamine epichlorohydrin resin, as described in U.S. Pat. No. 5,004,543 of Pluskal et al., the entire disclosure of which is herein incorporated by reference.

Hydrophilic membranes suitable for use in the present invention include membranes comprising polyamides such as nylons (e.g., nylon 66, nylon 6, nylon 610 or nylon 46); polyimides; polyesters; polyvinyl alcohols; polyvinylamines; polybenzylamides; polyvinylimidazolines; polydiallylamines; and mixtures thereof. Preferred hydrophilic membranes comprise neutral or slightly positively charged nylon polymers (e.g., Hybond™-N or Hybond™-NX blotting membranes, available from Amersham Biosciences, Piscataway, N.J.).

The charge carried by a nylon membrane is primarily determined by the type of compound added to terminate the synthetic reaction producing the nylon polymer. For example, if the termination compounds have carboxylic acid groups, the resulting nylon will be negatively charged. Likewise, if the termination compounds have amino groups, the resulting nylon will have a positive charge.

Typically, termination of the nylon synthetic reaction with amino-group containing compounds will produce a nylon polymer containing about 0.4 mole to about 2 moles amino groups per mole of nylon; membranes comprising such nylon polymers are preferred. For example, nylon membranes containing at least 0.9 mole amino end groups per mole of nylon, or at least 1.3 moles amino end groups per mole of nylon, are described in U.S. Pat. No. 5,458,782 of Hou et al., the entire disclosure of which is incorporated herein by reference. One of ordinary skill in the art can readily determine the amount of amino acid end groups per mole of nylon in a nylon membrane, for example by the methods disclosed in U.S. Pat. No. 5,458,782 of Hou et al., supra.

Membranes comprising highly positively charged nylons are known in the art, and are typically prepared by contacting a conventional nylon membrane with a solution containing a polyamine or polyamino-polyamine epichlorohydrin cation resin. Such highly positively charged nylon membranes will allow a certain amount of protein migration in the present electrophoretic methods, but generally do not produce adequate sample resolution (see Example 2 below). Therefore, highly positively charged nylon membranes are not preferred. In contrast, membranes comprising less positively charged nylons, as described in the preceding paragraph, and so-called "neutral" nylon membranes, produce good resolution of proteins by the present methods.

The polymeric membranes of the present invention typically have an average pore size of about 0.01 to about 5 microns, although membranes with larger or smaller pores can be used. Membranes with pore sizes between 0.05 and 1 micron are preferred, and membranes with pore sizes are between 0.1 and 0.5 microns are particularly preferred.

The membrane used in the present methods can be of any size (i.e., any length and width). A suitable membrane size for membrane electrophoresis is approximately 7.5 cm by 8 cm, although larger and smaller sizes can be used. For example, for high-throughput screening applications, the membrane can be cut into strips of approximately 1 cm by 8 cm. For extremely high resolution of separated proteins, or for separating large numbers of proteins, the membrane can be cut to 20 cm by 20 cm or larger. One of ordinary skill in the art can readily determine an appropriate membrane size for use in the present methods.

Membranes of the invention can be any thickness. Commercially available membranes are typically about 0.10 to about 0.15 mm thick, which thickness is suitable for separation of biological samples comprising up to 15 micrograms of protein. Samples containing larger quantities of proteins can also be separated. Membranes of other thicknesses, e.g., from about 0.01 mm to about 3 mm or greater are also contemplated for use in the present invention. Membranes with a thickness of about 0.05 mm to about 0.5 mm, for example about 0.1 mm to about 0.3 mm are particularly preferred.

Membrane electrophoresis can be carried out in any suitable electrophoresis apparatus to form an electrophoresis system of the invention. As used herein, an "electrophoresis apparatus" comprises at least one electrophoresis unit (often called a "gel box") for containing the buffer and membrane, and a power supply for generating an electric current in the electrophoresis unit.

Electrophoresis units are known in the art, and can be generally separated into units in which the separation substrate is oriented horizontally or vertically. The present membrane electrophoresis can be performed on either type of unit, but is preferably performed on a unit where the separation substrate is oriented horizontally (a "horizontal electrophoresis unit"). A horizontal electrophoresis unit useful in the present invention generally comprises two buffer reservoirs flanking a fixed platform on which the membrane separation substrate is placed. Electrodes are mounted in the buffer compartments, and the top of the unit is typically covered for safety purposes. The membrane must be in contact with the buffer in both buffer chambers, either directly or through a wick. The wick is typically made of filter paper. A current is produced in the electrophoresis unit by connecting a power supply to both electrodes and applying a voltage across the electrodes.

Electrophoresis units for use in the present invention can be constructed from any material which is compatible with the low conductivity organic solvent buffers described above. Generally, conventional electrophoresis units made from plastic or PlexiGlas® are not suitable for use in the present invention, as these materials are damaged by organic solvents. Electrophoresis units built of ceramics, teflon, glass or other materials resistant to organic solvents, or conventional PlexiGlas® or plastic electrophoresis units that are coated with organic solvent resistant materials (e.g., teflon or rubber), can be used.

A modified horizontal electrophoresis unit, generally designated as 100 in FIG. 1, was developed for the membrane electrophoresis system and methods. The unit comprises buffer chambers 110 and 110' located at opposite ends of the unit. Electrodes 120 and 120' are located adjacent to buffer chambers 110 and 110', respectively, so that the electrode leads 125 and 125' extend into the buffer chambers. The electrode leads, which are typically in the form of wires, can be any material capable of conducting electricity (e.g., platinum). A fixed, raised platform 130 separates the two buffer chambers, and prevents fluid communication between the chambers when they are filled with buffer.

In practice, at least one biological sample comprising proteins is spotted on high protein binding polymeric membrane 140, allowed to dry, and the membrane is wetted with the low conductivity organic solvent buffer. The membrane is then blotted to remove excess buffer, and placed directly on a filter paper wick 150 previously wetted with the same organic solvent buffer. The filter paper wick 150 rests on the platform 130. The membrane 140 can be coextensive in length and width with the platform 130, but usually is smaller in both length and width. In the embodiment shown in FIG. 1, the filter paper wick is longer than platform 130 so that either end of the wick extends into the buffer chambers. In a separate embodiment, the filter paper wick 150 can be replaced with two wicks, each of which overlaps with one end of membrane 140 and extends into a buffer chamber. In yet another embodiment, electrophoresis can be carried out with the membrane sandwiched between two plates without a wick or wicks. In this latter arrangement, both ends of the membrane extend into the two buffer chambers and act as wicks. In the first two embodiments discussed above, the wick or wicks draw buffer from the buffer chambers to the membrane, and help establish an electrical connection between the two buffer chambers through the membrane.

A top plate 160 is placed over, and is in direct contact with, the membrane. To prevent inadvertent electric shock during electrophoresis, a cover 170 is placed over the entire unit before voltage is applied across the electrodes. The top plate 160 and cover 170 can be made of any suitable non-electrically conductive material which is resistant to the organic solvent buffers; e.g., glass, ceramic, teflon, or PlexiGlas® coated with a material that is resistant to the organic solvent buffers. Preferably, top plate 160 and cover 170 are made of teflon or glass.

Figure 2:
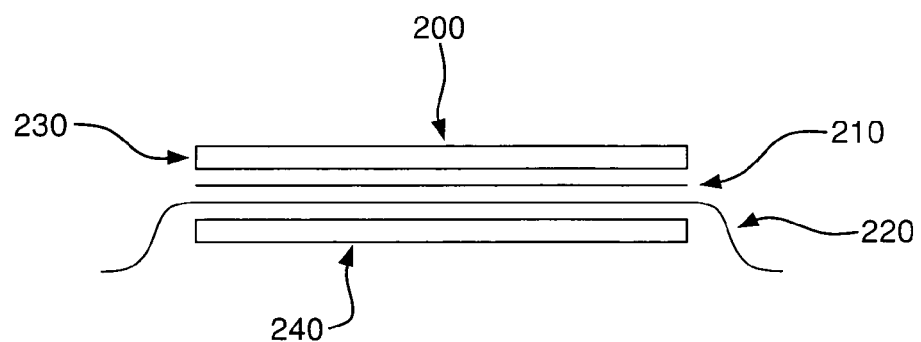
FIG. 2 is a side view of a "sandwich unit" containing a membrane and wick for use in horizontal electrophoresis units of the invention.

FIG. 2 shows an alternative arrangement for the membrane separation substrate and filter paper wick. In this arrangement, a membrane 210 and a filter paper wick 220 are sandwiched between top plate 230 and bottom plate 240 to form a "sandwich unit" generally designated as 200. The plates 230 and 240 are generally coextensive in length and width. The membrane 210 can be of variable size, but preferably has dimensions which are less than that of the plates 230 and 240. In the embodiment shown, the filter paper wick 220 has a greater length than the plates 230 and 240 so that wick material protrudes from the plates at either of the sandwich unit. The plates 230 and 240 can be made of any suitable non-electrically conductive material which is resistant to the organic solvent buffers; e.g., glass, ceramic, teflon, or PlexiGlas® coated with a material that is resistant to the organic solvent buffers. Preferably, the plates 230 and 240 are made of teflon or glass.

Referring again to FIG. 1, the sandwich unit 200 from FIG. 2 can be placed on platform 130 so that the ends of the filter paper wick extend into buffer chambers 110 and 110'.

Figure 3:
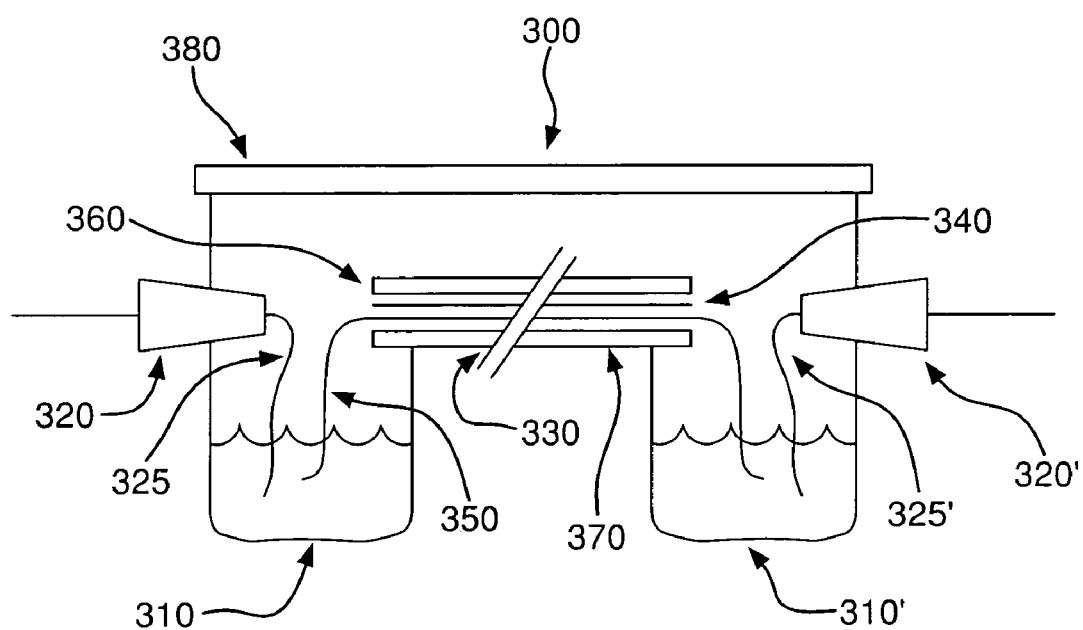
FIG. 3 is a side cutaway view of a variable length horizontal electrophoresis unit of the invention, showing two independent buffer chambers and a variable length sandwich unit.

Another embodiment of the electrophoresis unit is shown generally as 300 in FIG. 3. This unit comprises two independent buffer chambers 310 and 310'. Electrodes 320 and 320' are located adjacent to the buffer chambers, and have electrode leads 325 and 325' extending into the buffer chambers. There is no fixed platform between the buffer chambers; rather, a variable length sandwich unit 330 is used as the platform during electrophoretic separation. The sandwich unit 330 comprises a membrane 340 and filter paper wick 350 held between a top plate 360 and bottom plate 370. Because there is no fixed platform connecting the buffer chambers, the independent buffer chambers 310 and 310' can be spaced as appropriate to accommodate sandwich units of varying lengths. In practice, sandwich unit 330 is placed across appropriately spaced independent buffer chambers 310 and 310', such that either end of the filter paper wick is in contact with the buffer solution in the buffer chambers. A cover 380 is placed over the entire unit before voltage is applied across the electrodes. The plates 360 and 370 and cover 380 can be made of any suitable non-electrically conductive material which is resistant to the organic solvent buffers; e.g., glass, ceramic, teflon, or PlexiGlas® coated with a material that is resistant to the organic solvent buffers. Preferably, plates 360 and 370 and cover 380 are made of teflon or glass.

Any power supply capable of generating a voltage adequate to achieve the desired electric current can be used in the membrane electrophoresis systems and methods. Typical commercially available power supplies can generate a voltage of 3 to 4 kV, which is suitable for most membrane electrophoresis separations. Power supplies that can generate higher voltage, for example up to 75 kV, are also commercially available. One of ordinary skill in the art can readily obtain or construct power supplies capable of generating the required voltage for the present system and methods.

Membrane electrophoresis according to the present methods is generally performed as follows. Specific membrane electrophoresis protocols are described in the working examples below.

A polymeric membrane as described above is cut to the desired size. Generally, the membrane has no wells, indentations, or other surface features designed to hold the sample to be loaded. The biological samples comprising proteins to be separated are then loaded onto the membrane by any suitable technique; e.g., by "spotting" the samples onto the membrane with a transfer pipette or micropipette. For example, when loading samples onto hydrophobic membranes (e.g., PVDF), a wetting agent such as ε-caprolactone or dimethylformamide is added to the sample prior to application. The wetting agent may also contribute to the mobility of the proteins during electrophoresis. Preferably, the sample is allowed to dry on the membrane at room temperature. As discussed below, the proteins can move towards either electrode along the axis of the applied electric current. Thus, the samples are generally spotted on the membrane approximately midway between the two electrodes. Samples can also be spotted on other areas of the membrane to achieve specific separation. It is understood that multiple samples can be loaded onto a single membrane.

The membrane is then wetted in the low conductivity organic solvent buffer to be used for the electrophoretic separation. It is generally desirable to remove excess buffer from the membrane; e.g., by blotting with a paper towel. A filter paper wick previously wetted with the same organic solvent buffer is placed in position on the electrophoresis unit platform (or bottom glass plate, if a sandwich unit is being employed). The membrane is placed in position on the filter paper wick, and both buffer chambers are filled with electrophoresis buffer. A top glass plate is placed on top of the membrane containing the protein samples or mixtures. The electrophoresis unit is covered with a cover plate and the power supply is connected to the electrodes. With a power supply unit that generates high voltages, for example 75 kV, multiple electrophoresis units (e.g., 4 or more units) may be connected to a single power supply. The power supply is then switched on and the voltage output adjusted to achieve the desired current through the electrophoresis unit or units. Separation of the proteins in the sample begins upon application of electric current to the electrophoresis unit or units.

It is understood that the proteins migrate in a direction parallel to the membrane surface, as opposed to migrating in a direction which is perpendicular to the membrane surface. Without wishing to be bound by any theory, the protein in the samples are believed to migrate along the surface of the membrane during electrophoresis, and not through the membrane.

Again without wishing to be bound by any theory, separation of proteins by the present membrane electrophoresis methods apparently involves the weakening of the strong surface interactions between proteins in the sample and the protein binding membrane by the organic solvent buffers. This allows the proteins to migrate across the surface of the protein binding membrane when subjected to an electric current.

The amount of protein per sample that can be loaded onto the membrane will vary, and is influenced by factors such as the purity of the sample and the practical detection limit of the visualization or staining technique to be used. Generally, the amount of protein per sample can range from about 0.025 to about 15 micrograms. One of ordinary skill in the art can readily determine an appropriate amount of protein to be loaded onto the membrane.

Due to the organic character of the low conductivity electrophoresis buffer, samples comprising hydrophobic or low molecular weight (e.g., $M_r$<10,000) proteins, as well as samples comprising hydrophilic proteins, can be readily separated by the present methods.

Prior to loading, the samples can be mixed with substances which aid in the placement and retention of the samples on the membrane, or enhance the ability of the proteins to migrate upon electrophoresis. For example, the sample can be mixed with an equal volume of an organic solvent such as ε-caprolactone or dimethyl formamide before spotting onto a hydrophobic membrane. In particular, ε-caprolactone not only aids in the placement of the sample, but also improves the ability of proteins in the sample to migrate on membranes during membrane electrophoresis.

The sample can also be mixed with substances which aid in visualizing the extent of protein migration during the electrophoresis. Generally, such substances are dyes which migrate slightly before or along with the fastest migrating protein, although slower migrating substances can also be used. For example, the protein sample can be mixed with bromophenol blue, which typically migrates ahead of the fastest migrating protein. Fluorescent dyes such as acridine orange can also be used.

One or more proteins in the sample can also be labeled with a detection agent prior to loading onto the membrane. Suitable detection agents include colored dyes; fluorescent dyes; chemiluminescent labels; biotinylated labels, radioactive labels; affinity labels; enzyme labels; protein-specific antibodies; fluorescent antibodies and the like. Suitable fluorescent dyes include CyDye 2, 3 or 5 DIGE fluors available from Amersham Biosciences. In one embodiment, several samples, each containing a different fluorescently labeled protein, can be loaded onto the same membrane and electrophoresed. Alternatively, a single sample can comprise proteins labeled with different detection agents.

Other manipulations can also be performed on the samples prior to loading onto the membrane, including boiling or denaturing, mixing of the samples with suspected ligands, immunoprecipitation, and the like. In a preferred embodiment, samples are separated into hydrophilic and hydrophobic fractions prior to membrane electrophoresis. Sample separation can be carried out using an appropriate detergent. Detergents for separation of biological samples such as human serum into hydrophilic and hydrophobic fractions are well-known in the art. One such detergent is octylphenol ethoxylate, available as TRITON™ X-114.

Depending on the size of the membrane, electrophoresis is generally performed at about 1 to about 4 kV, although voltages as low as about 0.1 kV and as high as about 30 kV can be used. Preferably, the voltage used is about 2 kV to about 4 kV. The voltage is applied to the electrophoresis unit for an amount of time sufficient to separate the proteins which have been loaded onto the membrane. The time required for separating proteins varies, and is influenced by factors such as the voltage applied and the amount and complexity of the protein sample. Generally, the separation time can be shortened with the use of higher voltages (e.g., from about 10 to about 20 kV). One of ordinary skill in the art can readily determine an appropriate separation time for a given set of membrane electrophoresis conditions.

The current generated in the membrane electrophoresis methods should be in the range of about 0.0001 mA/cm² membrane to about 0.2 mA/cm² membrane, preferably 0.0005 mA/cm² membrane to about 0.05 mA/cm² membrane, more preferably about 0.001 mA/cm² membrane to about 0.025 mA/cm² membrane. When using a membrane of approximately 60 cm² (i.e., about 7.5 by 8 cm), currents of about 0.005 mA to about 5 mA, preferably about 0.01 mA to about 1.5 mA, more preferably about 0.03 mA to about 1.2 mA, particularly preferably about 0.05 to 1.0 mA, are generated. No significant heat is produced during membrane electrophoresis at currents below 1.5 mA.

Without wishing to be bound by any theory, migration of proteins on the membrane appears to be related to their isoelectric point ("pI"). For example, when the pH of the organic solvent buffer is equal to the pI of a protein molecule in the sample, that protein has a neutral charge and no migration of the protein is observed. However, if the pH of the organic solvent buffer is above the isoelectric point of a protein in the sample, that protein is positively charged and it migrates to the cathode. Likewise, proteins that are negatively charged in the buffer migrate towards the anode. The greater the difference between the pI of a protein and the pH of the buffer, the faster the migration of the protein.

Again without wishing to be bound by any theory, the molecular weight of the proteins does not appear to substantially influence migration during membrane electrophoresis.

In general, proteins within 5 pI units of the pH of the organic buffer can be separated. For example, an organic solvent buffer having a pH of 4.5 permits the separation of proteins with pI's ranging from about 1 to 9.6. Therefore, an organic solvent buffer with a pH of 8.5 can be expected to separate proteins with pI's of about 3.5 to as high as 12 or 13. It is understood, however, that proteins for which the difference between the pI and the buffer pH is greater than 5 units can also be separated by the present methods.

As used herein, the axis of protein migration along the membrane defines a "dimension." The axis of protein migration can be changed either by applying the electric current in a different direction relative to the orientation of the membrane, or by re-orienting the membrane in the original electric current. In one dimensional or "1-D" electrophoretic techniques, the axis of protein migration is not changed. For two dimensional or "2-D" techniques, the axis of protein migration is changed, for example, by turning the membrane in the electrophoresis unit.

Thus, in 1-D membrane electrophoresis techniques, proteins are separated only in a single dimension according to their isoelectric points, as influenced by the pH of the electrophoresis buffer. In 2-D membrane electrophoresis techniques, proteins are separated in a first dimension according to their isoelectric points as influenced by the pH of a first electrophoresis buffer, as in 1-D membrane electrophoresis. However, separation of the proteins in a second dimension is performed in a second buffer that has a pH value which is different from the first buffer. In practice, the membrane is typically removed from the electrophoresis unit after separation of the proteins in the first dimension, and is equilibrated in the second buffer. Preferably, the membrane is washed at least once; e.g., one to four times, in water to remove the first buffer before being equilibrated in the second buffer. For example, a suitable washing step can comprise placing the membrane in a tray of water with shaking for 20 minutes, with 3 to 4 changes of water within that time period.

If a wick is used, the first wick is usually discarded, and a second wick is equilibrated in the second buffer. The first buffer is also removed from the electrophoresis unit, and the buffer chambers are filled with the second buffer. The equilibrated membrane is then placed in the electrophoresis unit in a different orientation, and the electric current is re-applied. The different pH of the second buffer causes the proteins separated in the first dimension to become differently charged. Upon application of the electric current, the proteins migrate in the second dimension based on the pH of the second buffer. As can be seen in Example 4, high resolution separation of a large number of proteins can be achieved with the 2-D membrane electrophoresis method.

It is understood that the first and second buffers for use in 2-D membrane electrophoresis can have the same composition, but a different pH. For example, the pH of the first and second buffers can be adjusted as described in Example 1 below. Alternatively, the first and second buffers can have a different composition and a different pH.

When analyzing protein samples obtained from different time points by 2-D membrane electrophoresis, it is preferable to use larger protein-binding membranes, for example 20 cm×20 cm, as multiple samples can be applied to different regions of the membrane and run simultaneously.

The present membrane electrophoresis methods also comprise "pulsed-field" electrophoresis techniques, such as are known in the art.

After the proteins have been separated by membrane electrophoresis, they can be visualized as protein spots on the membrane with standard staining or detection techniques. Such techniques include colorimetric protein detection methods (e.g.; employing Ponceau S, Coomassie blue, or amido black); colloidal gold staining; silver staining coupled with silver enhancement; immunostaining, chemiluminescent detection, fluorescent imaging; radioimaging, and the like, as are known in the art. Staining or detection techniques which are highly sensitive are preferred. For example, colloidal gold staining can detect approximately 1 to 2 nanograms (ng) of protein on a membrane, and silver staining coupled with silver enhancement can detect approximately 0.5 ng protein on a membrane. However, the colloidal gold staining takes up to 2 hours to complete and does not stain proteins separated on all types of membranes with equal sensitivity (Pluskal et al., *Biotechniques* 4:272-283, 1986). Silver staining coupled with silver enhancement is also very time consuming and difficult to perform.

A novel and highly sensitive protein staining method using the Reactive Brown fabric dye has been developed. The Reactive Brown staining method is particularly suited to detecting proteins separated by membrane electrophoresis, and is the subject of the commonly owned International Patent Application publication no. WO 2004/025253, titled "Method of Visualizing Proteins Bound to Protein Binding Membranes," filed on Sep. 9, 2003 and published on Mar. 25, 2004, and corresponding United States Patent Application publication no. 2005/0214735, published Sep. 29, 2005. The entire disclosures of the aforesaid patent documents are incorporated herein by reference in their entireties. This method can rapidly detect proteins separated by membrane electrophoresis down to about 1 ng, with approximately equal sensitivity on the various types of polymeric membranes described above. At this level of sensitivity, it is possible to resolve several hundred protein spots separated on a 7.5 cm×8 cm membrane according to the present methods.

In one embodiment, the membrane electrophoresis can be conducted under non-denaturing conditions (e.g., in the absence of urea or SDS). Under non-denaturing conditions, protein-binding interactions and protein complexes are retained during and after electrophoresis. Other methods within the skill in the art can be used to identify proteins separated by the present methods under non-denaturing conditions, including sequencing or immunodetection with protein-specific antibodies (e.g., Western analysis).

Proteins electrophoresed with the present methods under non-denaturing conditions can retain enzymatic activities. The separated proteins or protein complexes retaining the enzymatic activity of interest can be detected by any suitable method, for example by zymographic analysis directly on membrane. Zymographic analysis can be carried out, for example, with colorimetric or fluorogenic substrates.

Membrane electrophoresis under non-denaturing conditions also provides a simple method for identification of proteins in the protein spots. The nature of the proteins in the protein spots can be determined by using protein-specific antibodies, enzymatic analysis, mass spectrometric analysis, protein sequencing and the like, according to procedures within the skill in the art.

The invention will now be illustrated by the following non-limiting examples.

General Materials and Methods:

Human Serum Samples: Serum samples were obtained from normal subjects, subjects with pancreatic disease, and subjects with cancer by standard techniques. The subjects with cancer included subjects with breast cancer, liver cancer, skin cancer, and pancreatic cancer, diagnosed at Georgetown University, the University of Georgia, and Temple University.

Two-Dimensional Membrane Electrophoresis: Low conductivity organic solvent buffers were formulated as follows:

Buffer A—The conductivity enhancers salicylaldehyde and furfuryl alcohol were added to the base solvent ethylene cyclic carbonate. The conductivity suppressors 1,3-butanediol, dimethyl formamide and dimethyl acetamide were added to reduced current and eliminate heat generation, with minimal reduction in protein migration rates. The final formulation of Buffer A was 28% ethylene cyclic carbonate, 16% salicylaldehyde, 12% furfuryl alcohol, 8% 1,3-butanediol, 20% dimethylformamide, and 16% dimethylacetamide.

The pH of Buffer A was adjusted to 4.5 with 12 M formic acid, although pHs in a range of about 3 to about 6 can be achieved by varying the amount of formic acid added. In addition, the pH of Buffer A can be adjusted in the range of about 6 to about 10 by adding 0.5 M piperazine dissolved in furfuryl alcohol.

Buffer B—The conductivity enhancers formamide and furfuryl alcohol were added to the base solvent propylene carbonate. The addition of a mixture of the conductivity suppressors 1,3-butanediol and N-methyl pyrrolidinone reduced the current to 0.3 mA and eliminated the heat generation with only a minimal effect on protein migration. The final formulation of Buffer B was: 44% propylene carbonate, 12% formamide, 12% furfuryl alcohol, 16% 1,3-butanediol, and 16% N-methyl pyrrolidinone. The pH of the buffer was brought to 8.5 with 0.5 M piperazine, although pH's in the range of about 6 to about 10 can be achieved by varying the amount of piperazine added.

Four microliters of fractionated serum containing 40 µg of total protein were mixed with 4 µl of ε-caprolactone and 0.5 µl of the resulting mixture was spotted at the middle of a PVDF blot membrane (9 cm×13 cm) and allowed to air dry. If necessary another 0.5 µl of the same sample can be applied on the same spot. The membrane electrophoresis was performed on a modified horizontal electrophoresis apparatus with the glass plate "sandwich unit" arrangement essentially as shown in FIG. 1. The membrane was soaked briefly in Buffer A and blotted to remove any excess solvent. The membrane was placed on top of a long filter paper wick, and the wick and membrane were sandwiched in between the two glass plates. The wick was longer than the membrane and the glass plates, and the ends of the wick protruded from the glass plates. This "sandwich unit" was positioned on the raised platform of the horizontal electrophoresis unit so that the ends of the wick extended into filled buffer compartments. A protective glass cover was placed over the top of the unit, and a power supply was connected to the platinum electrodes of the electrophoresis unit. The fractionated serum samples were separated in the first dimension at 3.5 kV for 6 minutes, generating a current of about 0.1 mA, using Buffer A (pH 4.5).

Upon completion of the first dimension separation, the membrane was marked to ensure proper orientation, and washed for several minutes in deionized $H_2O$ to remove the first dimension solvents. A new filter paper wick was equilibrated with the second dimension Buffer B (pH 8.5) and was placed on top of the bottom plate. After equilibration with the second dimension solvent, the membrane was then placed on top of the new filter paper wick turned 90° from its original position and covered with a top plate. The second dimension separation was carried out at 3.5 kV for 6 minutes generating a current of about 0.3 mA both first and second dimension separations were carried out at room temperature without cooling.

At the end of the second dimension separation, the membrane was removed, washed with water and stained with the Reactive Brown dye according to the method disclosed in the commonly owned International Patent Application publication no. WO 2004/025253 and corresponding United States Patent Application publication no. 2005/0214735, supra.

Mass Spectrometry: To identify the protein components of spots resolved by two-dimensional membrane electrophoresis, various mass spectrometric techniques were used. First, protein spots of interest which had been resolved by two-dimensional membrane electrophoresis were cut from the membrane. Proteins were eluted from the membrane and prepared for of mass spectrometry using a combination of liquid chromatography and tandem mass spectrometry (LC-MS/MS) procedures, in order to separate, ionize, and analyze the proteins.

Example 1

Separation of Human Serum into Hydrophilic and Hydrophobic Fractions

To eliminate the crowding of protein complex spots, serum samples were separated into hydrophilic and hydrophobic fractions by using the detergent Triton X-114 before electrophoresis.

Methods: The Bordier procedure (Bordier, 1981, J. Biol. Chem. 256:1604-1607, the entire disclosure of which is herein incorporated by reference) for separation of membrane proteins was modified to separate human serum into hydrophilic and hydrophilic fractions. Specifically 5.0 µl of human serum from a normal (non-cancerous) subject were mixed with 150 µl of 10 mM Tris-HCl buffer (pH 8.0) containing 0.15 M NaCl and 1% Triton X-114 in an Eppendorf microfuge tube, and the mixture was placed on ice for 15 minutes. The mixture was then incubated in a 37° C. water bath for 30 minutes and spun at 1,000×g for 5 minutes in a microfuge. About 100 µl of the top layer (hydrophilic fraction) was removed and transferred to a new microfuge tube. The remaining hydrophobic material was removed without disturbing the oily droplet consisting of the hydrophobic fraction in Triton X-114. The oily droplet at the bottom of the tube was washed with 150 µl of the same Tris buffer (see above), but without Triton X-114. Following the wash, the oil droplet was spun at 1,000×g for 5 minutes, and the supernatant fraction was carefully removed by a pipette.

To remove the detergent and salt from the fractionated samples, 40.0 μl of the hydrophilic fraction and about 10 μl of the hydrophobic fraction were loaded separately onto Bio-Gel P-6 columns (Bio-Rad, Hercules, Calif.) according to the manufacturer's instructions. The desalted hydrophilic and hydrophobic fractions (5 μl each) were then separately mixed with 5.0 μl of s-caprolactone. 0.5 μl of the resulting mixture was applied separately at the middle of a PVDF blot membrane (9 cm×13 cm) and allowed to air dry. If necessary another 0.5 μl of the same sample can be applied on the same spot. The membranes were then subjected to two-dimensional membrane electrophoresis as described above.

Results: Two-dimensional electrophoretic analysis of hydrophilic and hydrophobic serum fractions from a non-cancerous subject demonstrated that proteins of the hydrophilic serum fraction were separated into well-resolved spots (FIG. 4A), as were proteins of the hydrophobic fraction (FIG. 4B). The electrophoretic procedure required only about 40 minutes and less than 5.0 μl of serum. Both hydrophilic and hydrophobic protein complexes (FIGS. 4A and 4B) were separated into very compact and distinct spots without streaking or diffusion normally found in the conventional 2-D PAGE system.

Figure 4A:
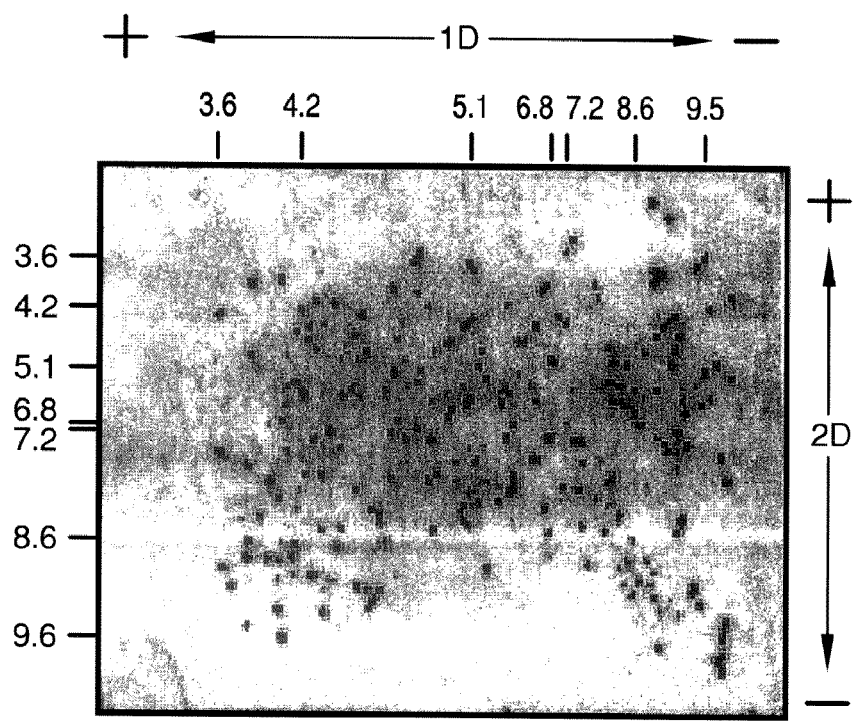
FIGS. 4A and 4B represent two-dimensional membrane electrophoretic separation profiles of hydrophilic (FIG. 4A) and hydrophobic (FIG. 4B) fractions of serum from a normal individual. The first dimension (1-D) and second dimension (2-D) directions are indicated by arrows. The orientation of the membranes with respect to the positive and negative electrodes during electrophoresis is indicated by "+" and "−".
Figure 4B:
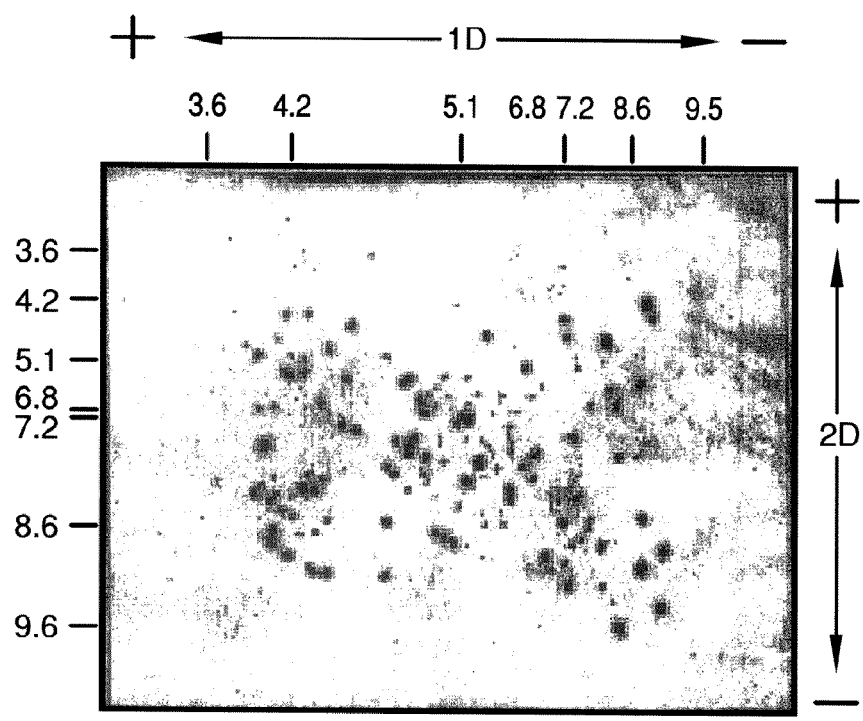

FIGS. 4A and 4B also show an absence of serum albumin spots because the samples were separated under non-denaturing conditions. Serum albumins, which constitute approximately 50% of total serum proteins, are in fact distributed in many of the resolved spots because albumins interact with and form complexes with many proteins. Mass spectrometric analyses of four randomly chosen spots from the separated hydrophilic fraction (FIG. 4A) indicated that each spot contains serum albumin and at least ten other proteins.

Example 2

Figures 5A, 5B:
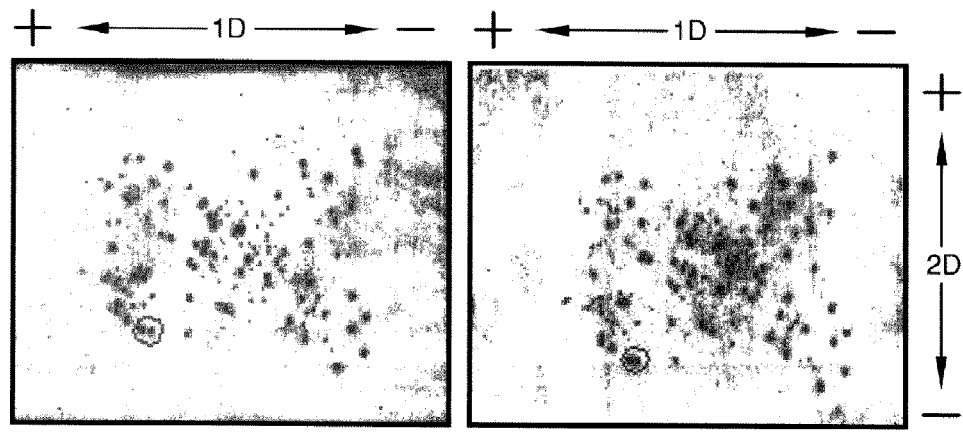
FIGS. 5A, 5B, 5C, and 5D are representative two-dimensional membrane electrophoretic profiles of hydrophobic serum fractions of normal individuals (FIGS. 5A and 5B) and subjects with pancreatic cancer (FIGS. 5C and 5D) electrophoresed on PVDF membranes. The first dimension (1-D) and second dimension (2-D) directions are indicated by arrows. The orientation of the membranes with respect to the positive and negative electrodes during electrophoresis is indicated by "+" and "−". Encircled areas indicate regions of protein marker changes.

Identification of Pancreatic Cancer Markers in the Hydrophobic Fraction of Serum Hydrophobic serum fractions from eleven different subjects with pancreatic cancer were prepared as described above (Example 1) and subjected to two-dimensional membrane electrophoresis. The hydrophobic serum fraction of pancreatic cancer exhibited a unique separation profile compared to the hydrophobic serum fraction electrophoretic profile of normal subjects. For example, the data demonstrate that a cluster of about ten protein spots (or protein complexes) appeared in all samples from subjects with pancreatic cancer (FIGS. 5C and 5D), whereas in normal subjects only two of the ten proteins (or protein complexes) were present (FIGS. 5A and 5B). The data also show that other protein spots were unique to the samples from subjects with pancreatic cancer (FIGS. 5A-5D).

Example 3

Analysis of the Nature of Pancreatic Cancer Markers

An experiment was performed to demonstrate that protein spots or clusters on a membrane electrophoresis separation profile can be expanded to help resolve individual protein components of the protein spots or clusters. An aliquot of the hydrophobic fraction of a serum sample from a subject with pancreatic cancer was spotted at the center of a PVDF membrane, as described in Example 1. An aliquot of the same hydrophobic serum fraction was also spotted at the upper right corner of a PVDF membrane, instead of in the middle of the membrane. Both aliquots were then subjected to two-dimensional membrane electrophoresis. The electrophoretic profile of FIG. 6B demonstrates that the spots in the cluster outlined in FIG. 6A, as well as spots adjacent to the cluster, were resolved into more easily identifiable spots by initiating electrophoresis of the sample in a different region of the membrane.

Seven pancreatic cancer-specific spots were identified and labeled as spots 1 to 7 in FIG. 6B. To identify the protein components of the seven pancreatic cancer-specific spots identified in FIG. 6B, the seven spots were cut from the PVDF membrane and the proteins were eluted from the membrane. The eluted samples were trypsinized and the proteins were analyzed by mass spectrometry (LC/MS/MS). Protein spots 1, 2, 3, and 4 were found to contain tumor-specific pyruvate kinases forming complexes with other proteins, such as serum albumin and aldolases. Protein spots 5, 6, and 7 were found to contain a complex of core proteins comprising serum albumin, apolipoprotein A-1, histidine-rich glycoprotein, and paroxonase 1. In addition, protein spot 5 of FIG. 6B was found to contain, in addition to the complex of core proteins described above, other proteins such as alpha-1-trypsin inhibitor, vitamin D-binding protein, actin, and fetuin.

Example 4

Identification of Pancreatic Cancer Markers in the Hydrophilic Serum Fraction

Figures 7A, 7B:
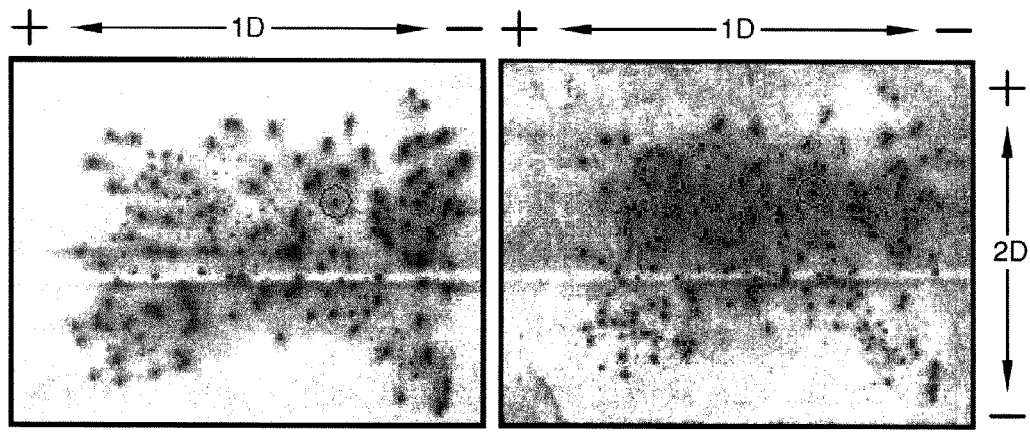
FIGS. 7A to 7D represent two-dimensional membrane electrophoretic separation profiles of hydrophilic serum fractions of normal individuals (FIGS. 7A and 7B) and subjects with pancreatic cancer (FIGS. 7C and 7D). The first dimension (1-D) and second dimension (2-D) directions are indicated by arrows. The orientation of the membranes with respect to the positive and negative electrodes during electrophoresis is indicated by "+" and "−". Encircled areas indicate regions of protein marker changes.
Figures 7C, 7D:
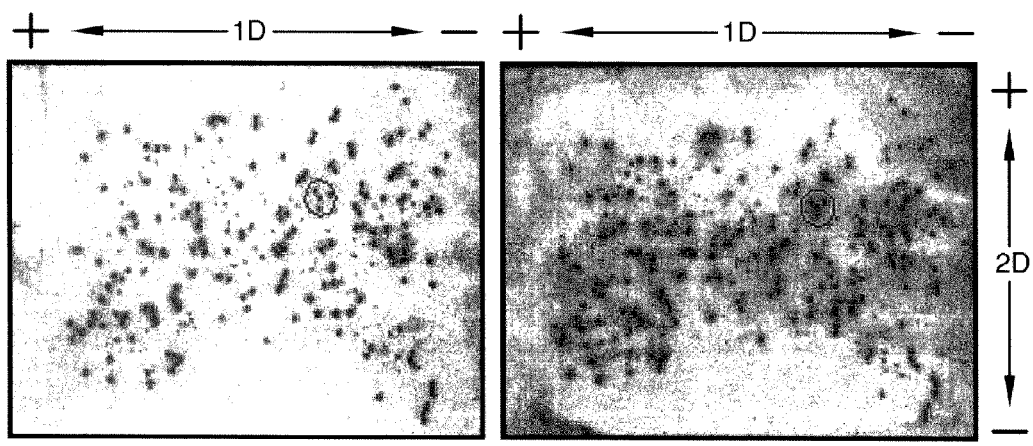

Hydrophilic fractions prepared from the serum of subjects with pancreatic cancer were compared to hydrophilic serum fractions from normal subjects by two-dimensional membrane electrophoresis. FIGS. 7A and 7B are representative two-dimensional membrane electrophoretic profiles of hydrophilic serum fractions from two different normal subjects. FIGS. 7C and 7D are representative two-dimensional membrane electrophoretic profiles of hydrophilic serum fractions from two different subjects with pancreatic cancer. A region is circled in each of the electrophoretic profiles of FIGS. 7A to 7D, indicating the pancreatic cancer-specific markers (FIGS. 7C and 7D). These markers are absent from the serum of normal subjects (FIGS. 7A and 7B). In each of the samples from subjects with pancreatic cancer (FIGS. 7C and 7D), it can be seen that three additional proteins spots or markers are identifiable.

The two-dimensional membrane separation profiles indicate that there are more pancreatic cancer markers in the hydrophobic serum fraction than in the hydrophilic serum fraction of subjects with pancreatic cancer (see Example 2, FIGS. 5A-5D and 7A-7D). Although there are identifiable pancreatic cancer markers in the hydrophilic fraction of serum (FIGS. 7C and 7D), the hydrophilic fraction profiles are more similar to profiles from normal subjects, than are the separation profiles of the hydrophobic serum fractions of subjects with pancreatic cancer (FIGS. 5A-5D).

Example 5

Figures 5C, 5D:
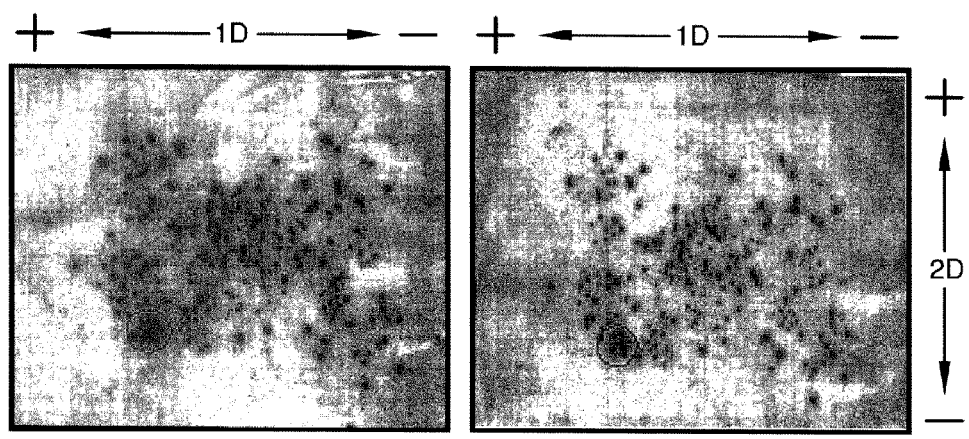
Figure 8A:
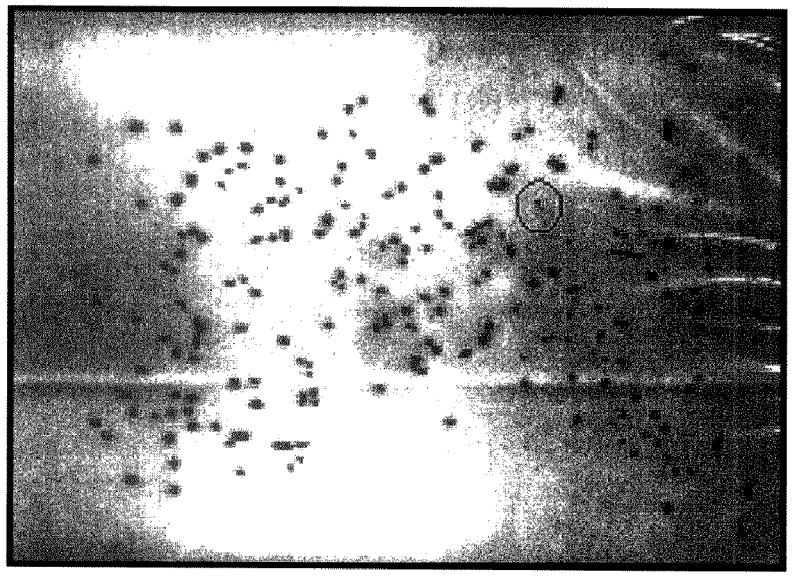
FIGS. 8A and 8B represent two-dimensional membrane electrophoretic separation profiles of hydrophilic (FIG. 8A) and hydrophobic (FIG. 8B) fractions of serum obtained from subject with pancreatitis. Encircled areas indicate regions of protein marker changes.
Figure 8B:
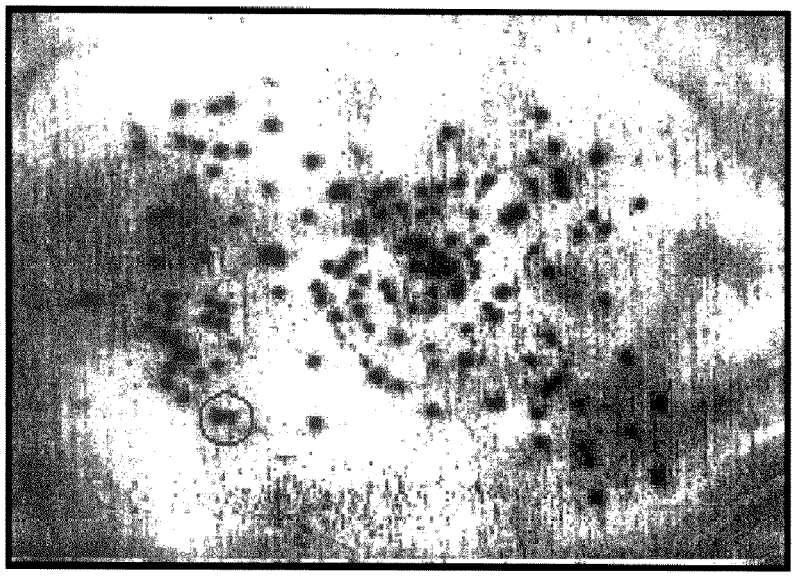
Figure 10A:
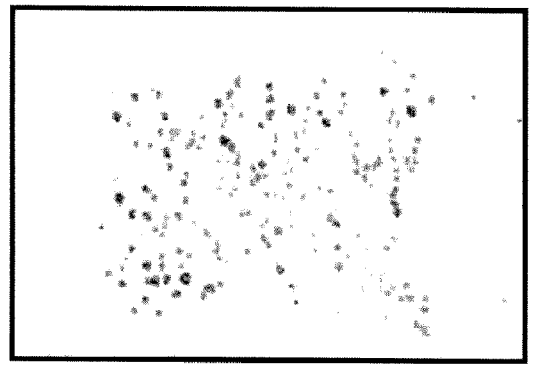
FIGS. 10A to 10E represent two-dimensional membrane electrophoretic separation profiles of hydrophilic fractions of serum derived from: a normal subject (FIG. 10A), or subjects with Stage I breast cancer (FIG. 10B), Stage II breast cancer (FIG. 10C), Stage III breast cancer (FIG. 10D) and Stage IV breast cancer (FIG. 10E).
Figure 10B:
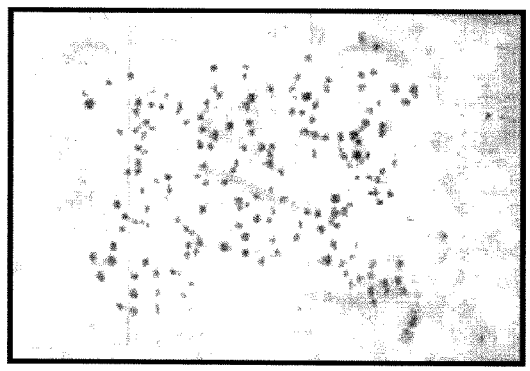
Figure 10C:
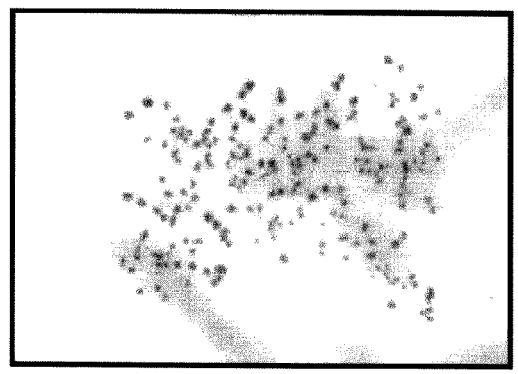
Figure 10D:
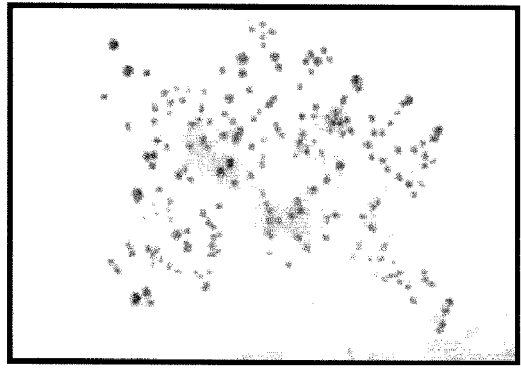
Figure 10E:
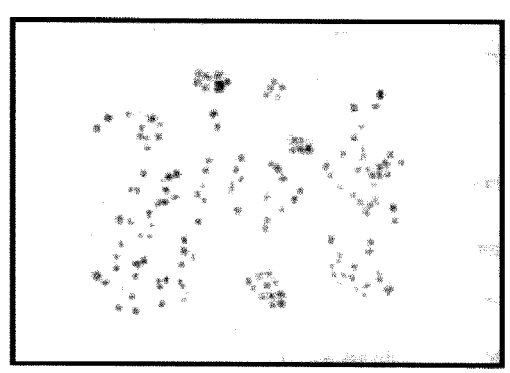

Absence of Pancreatic Cancer Markers in the Serum of Patients Suffering from Non-Cancerous Pancreatic Diseases To further evaluate the specificity of the pancreatic cancer markers identified in hydrophilic and hydrophobic serum fractions of subjects with pancreatic cancer, serum fractions from patients with pancreatitis were subjected to two-dimensional membrane electrophoresis (FIGS. 8A and 8B). The data show that the two-dimensional membrane separation profile of the hydrophilic serum fraction from subjects with pancreatitis (FIG. 8A) is similar to the profile of the hydrophilic serum fraction of normal subjects (FIGS. 4A, 7A and 7B), in neither profile has the pancreatic cancer markers identified in the hydrophilic serum fraction from subjects with pancreatic cancer (FIGS. 7C and 7D). In addition, the hydrophobic serum fraction of pancreatitis patients (FIG. 5B) is similar to the hydrophobic serum fraction from normal subjects (FIGS. 4B, 5A and 8B), in that it does not have the pancreatic cancer markers identified in the hydrophobic serum fraction from subjects with pancreatic cancer (FIGS. 5C and 5D). Therefore, the data indicate that the pancreatic cancer markers identified herein are unique to pancreatic cancer and are not general markers of pancreatic disease or insult.

Example 6

Identification of Stage-Specific Breast Cancer Markers in the Hydrophobic Serum Fraction of Cancer Patients Serum samples were obtained from at least three subjects for each of the four breast cancer stages (i.e., Stages I-IV). Serum was also obtained from normal (non-cancerous) subjects.

The histological subtypes of the breast cancers included ductal and lobular adenocarcinoma. Estrogen receptor status was not determined for all breast tumors of subjects whose blood was used in this study, but serum samples were obtained from subjects with estrogen receptor-positive and -negative breast tumors The subjects included pre-, peri-, and post-menopausal women. Some subjects had been treated with tamoxifen.

Serum samples from normal and test subjects were separated into hydrophilic and hydrophobic fractions and subjected to two-dimensional membrane electrophoresis as described above (Example 1). Representative two-dimensional membrane electrophoretic profiles of hydrophobic fractions of serum are provided in FIGS. 9A (normal), 9B (Stage I breast cancer), 9C (Stage II breast cancer), 9D (Stage III breast cancer) and 9E (Stage IV breast cancer), and demonstrate that new proteins (or protein complexes) appear at each new stage of cancer progression. The separation profiles showing stage-specific protein markers are reproducible, as determined by analysis of multiple patients from each breast cancer stage.

The data demonstrate that a cluster of about twelve proteins (or protein complexes) appeared in the middle left side of the separation profile of samples from subjects with Stage I breast cancer (FIG. 9B), relative to normal subjects (FIG. 9A). Another cluster of four new protein spots also appeared in the top of the profile in samples from Stage I subjects (FIG. 9B).

In samples from subjects with Stage II breast cancer (FIG. 9C), the cluster of four new protein spots seen in Stage I patients was still identifiable. In addition, a new cluster of about 10 proteins (or protein complexes) appeared in Stage II subjects.

In samples from subjects with Stage III breast cancer, a new cluster of about nine protein spots (or protein complexes) appeared (FIG. 9D), compared to samples from normal subjects (FIG. 9A) or earlier stages of breast cancer (FIGS. 9B and 9C). In addition, the cluster of four new proteins which appeared in samples from Stage I and Stage II breast cancer subjects was modified as the subjects progressed to Stage III breast cancer. That is, two of the four proteins in the cluster seen in this Stage III breast cancer separation profile had different electrophoretic mobilities than the protein spots in the same cluster in the Stage I and Stage II separation profiles.

In samples from subjects with Stage IV breast cancer (metastatic cancer), a new cluster of about six protein spots was identifiable (FIG. 9E), compared to normal subjects and to subjects with earlier stages of breast cancer (FIGS. 9A to 9D). In addition, two of the proteins present in the four-protein cluster of the separation profiles of the Stage I and III were no longer present in the Stage IV breast cancer separation profile. Thus, specific serum markers indicative of specific breast cancer stages were identified using the methods described herein.

Example 7

Identification of Breast Cancer Markers in the Hydrophilic Serum Fraction

Hydrophilic serum fractions were obtained from subjects with (Stages I, II, III, and IV) breast cancer as described above (see Example 6). The serum samples were fractionated into hydrophilic and hydrophobic fractions and subjected to two-dimensional membrane electrophoresis as described above. Analysis of the fraction shows that stage-specific protein markers also appear in the hydrophilic serum fractions of subjects with breast cancer (FIGS. 10A to 10E).

Example 8

Identification of Specific Markers for Melanoma

Figure 11A:
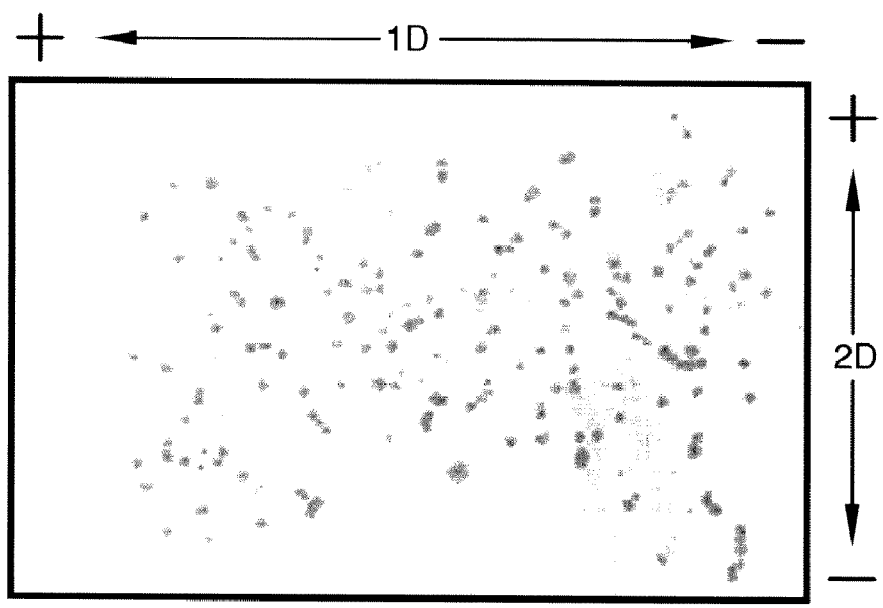
FIGS. 11A and 11B represent two-dimensional membrane electrophoretic separation profiles of hydrophilic (FIG. 11A) and hydrophobic (FIG. 11B) serum fractions obtained from a subject with skin cancer (melanoma). The first dimension (1-D) and second dimension (2-D) directions are indicated by arrows. The orientation of the membranes with respect to the positive and negative electrodes during electrophoresis is indicated by "+" and "−". Encircled areas indicate regions of protein marker changes.
Figure 11B:
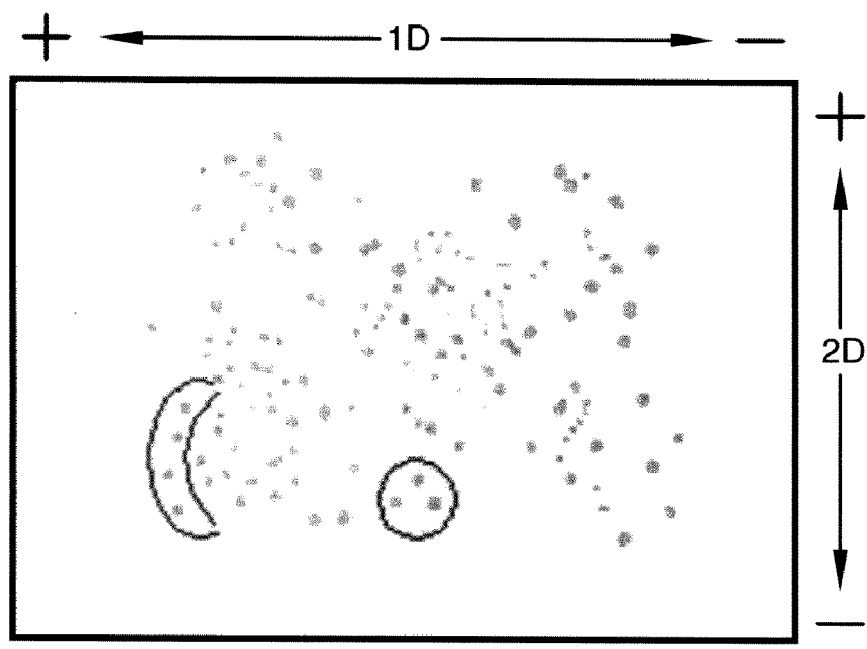

Serum was obtained from subjects with the skin cancer melanoma. The serum was fractionated into hydrophilic and hydrophobic fractions and subjected to two-dimensional membrane electrophoresis as described above. Analysis of the hydrophilic and hydrophobic serum fractions of subjects with melanoma showed that markers specific for melanoma were present primarily in the hydrophobic serum fraction of the melanoma subjects (see FIGS. 11A and 11B). Two regions where protein marker changes occurred are indicated in the hydrophobic serum fraction profile (FIG. 11B).

Example 9

Identification of Specific Markers for Hepatocellular Carcinoma

Figure 12A:
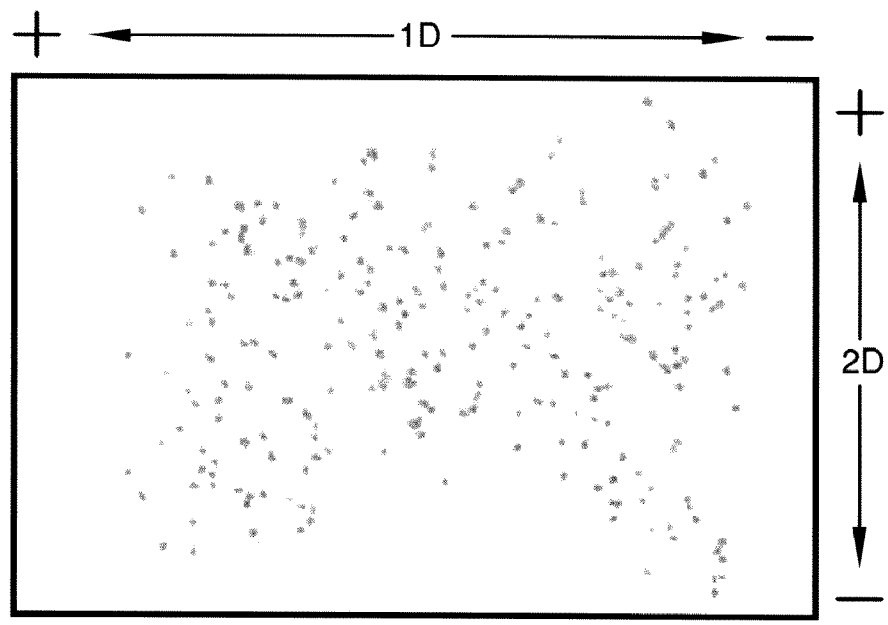
FIGS. 12A and 12B represent two-dimensional membrane electrophoretic separation profiles of hydrophilic (FIG. 12A) and hydrophobic (FIG. 12B) serum fractions obtained from a subject with hepatocellular carcinoma. The first dimension (1D) and second dimension (2D) directions are indicated by arrows. The orientation of the membranes with respect to the positive and negative electrodes during electrophoresis is indicated by "+" and "−". Encircled areas indicate regions of protein marker changes.
Figure 12B:
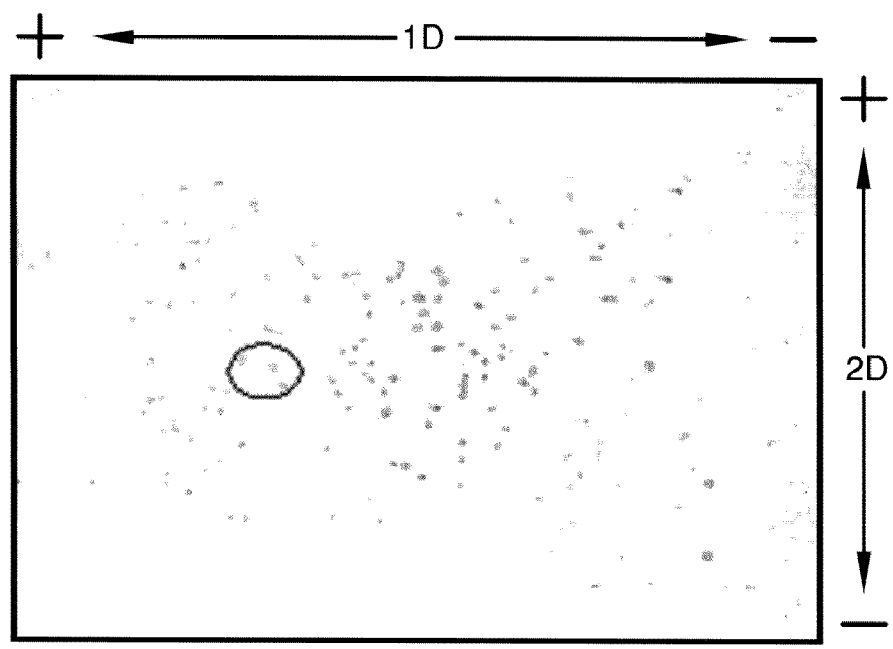

Serum was obtained from subjects with hepatocellular carcinoma. The serum was fractionated into hydrophilic and hydrophobic fractions and subjected to two-dimensional membrane electrophoresis as described above. FIG. 12 shows that markers for hepatocellular carcinoma were present in the hydrophobic serum fraction from hepatocellular carcinoma subjects (FIG. 12B), relative to the hydrophilic serum fraction (FIG. 12A) of those subjects or to serum fractions from normal subjects (FIGS. 4A, 4B, 5A, 5B, 7A, 7B, 9A, and 10A).

All documents referred to herein are incorporated by reference. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

We claim:

1. A method of identifying disease-specific markers in a biological sample, comprising:
   (1) obtaining at least one biological sample comprising proteins and protein complexes from at least one normal subject;
   (2) obtaining at least one biological sample comprising proteins and protein complexes from at least one diseased subject;
   (3) separating the proteins and protein complexes in the at least one biological sample provided in step (1) by membrane electrophoresis to obtain a normal separation profile;
   (4) separating the proteins and protein complexes in the at least one biological sample obtained in step (2) by membrane electrophoresis to obtain a disease separation profile comprising disease-specific protein and protein complex clusters; and
   (5) comparing the normal separation profile to the disease separation profile to determine the difference in the number and distribution of proteins and protein complex clusters between the normal and disease separation profiles,
   wherein the difference in the number, distribution or both number and distribution of proteins and protein complex clusters between the normal and disease separation profiles represents the disease-specific markers.

2. The method of claim 1, wherein the disease is cancer, a neurological disease, or heart disease.

3. The method of claim 2, wherein the cancer is breast cancer, pancreatic cancer, melanoma, or hepatocellular carcinoma.

4. The method of claim 2, wherein the neurological disease is Alzheimer's disease, multiple sclerosis, Parkinson's disease, or migraine headaches.

5. The method of claim 1, wherein the biological sample comprises a biological fluid.

6. The method of claim 5, wherein the biological fluid is selected from the group consisting of blood, serum, saliva, urine, lymph, perspiration, mucus, cerebro-spinal fluid, lachrymal fluid, vitreous humor, semen, vaginal secretions, and mammary gland secretions.

7. The method of claim 1, Wherein the biological sample comprises the hydrophobic fraction of a biological fluid.

8. The method of claim 1, wherein the biological sample comprises the hydrophilic fraction of a biological fluid.

9. A method of diagnosing a disease in a test subject, comprising:
   (1) obtaining at least one biological sample comprising proteins and protein complexes from the test subject;
   (2) separating the proteins and protein complexes in the at least one biological sample by membrane electrophoresis to obtain a test separation profile;
   (3) providing a standard separation profile representing the disease to be diagnosed comprising disease-specific protein and protein complex clusters; and
   (4) comparing the test separation profile to the standard separation profile,
   wherein a substantial similarity between the number and distribution of proteins and protein complex clusters in the test separation profile and the standard separation profile indicates that the test subject has the disease represented by the standard separation profile.

10. The method of claim 9, wherein the disease is cancer, a neurological disease or heart disease.

11. The method of claim 10, wherein the cancer is breast cancer, pancreatic cancer, melanoma, or hepatocellular carcinoma.

12. The method of claim 10, wherein the neurological disease is Alzheimer's disease, multiple sclerosis, Parkinson's disease, or migraine headaches.

13. The method of claim 9, wherein the biological sample comprises a biological fluid.

14. The method of claim 13, wherein the biological fluid is selected from the group consisting of blood, serum, saliva, urine, lymph, perspiration, mucus, cerebro-spinal fluid, lachrymal fluid, vitreous humor, semen, vaginal secretions, and mammary gland secretions.

15. The method of claim 9, wherein the biological sample comprises the hydrophobic fraction of a biological fluid.

16. The method of claim 9, wherein the biological sample comprises the hydrophilic fraction of a biological fluid.

17. The method of claim 9 wherein said disease is diagnosed as cancer, further comprising staging said cancer by a method comprising:
   (1) obtaining at least one second biological sample comprising proteins and protein complexes from the test subject;
   (2) separating the proteins and protein complexes in the at least one second biological sample by membrane electrophoresis to obtain a second test separation profile comprising disease-specific protein and protein complex clusters;
   (3) comparing the second test separation profile to a set of standard separation profiles comprising a plurality of stage-specific separation profiles to determine whether one of the stage-specific separation profiles is substantially similar to the second test separation profile,
   wherein the test subject has cancer of the stage represented by the stage-specific separation profile which is substantially similar to the second test separation profile.

18. A method of staging cancer in a test subject, comprising:
   (1) obtaining at least one biological sample comprising proteins and protein complexes from the test subject;
   (2) separating the proteins and protein complexes in the at least one biological sample by membrane electrophoresis to obtain a test separation profile comprising disease-specific protein and protein complex clusters;
   (3) comparing the test separation profile to a set of standard separation profiles comprising a plurality of stage-specific separation profiles comprising disease-specific protein and protein complex clusters to determine whether one of the stage specific separation profiles is substantially similar to the test separation profile,
   wherein the test subject has cancer of the stage represented by the stage specific separation profile which is substantially similar to the test separation profile.

19. The method of claim 18, wherein the cancer is breast cancer, pancreatic cancer, melanoma, or hepatocellular carcinoma.

20. The method of claim 18, wherein the biological sample comprises a biological fluid.

21. The method of claim 20, wherein the biological fluid is selected from the group consisting of blood, serum, saliva, urine, lymph, perspiration, mucus, cerebro-spinal fluid, lachrymal fluid, vitreous humor, semen, vaginal secretions, and mammary gland secretions.

22. The method of claim 18, wherein the biological sample comprises the hydrophobic fraction of a biological fluid.

23. The method of claim 18, wherein the biological sample comprises the hydrophilic fraction of a biological fluid.

24. A method of determining the prognosis of a subject with cancer, comprising determining the stage of cancer in the subject according to claim 18, wherein the prognosis of the subject decreases with increasing cancer stage.

25. A method of staging breast cancer in a test subject, comprising;
   (1) obtaining at least one biological sample comprising proteins and protein complexes from the test subject;
   (2) separating the proteins and protein complexes in the at least one biological sample by membrane electrophoresis to obtain a test separation profile comprising stage-specific protein and protein complex clusters; and
   (3) comparing the test separation profile to a set of standard separation profiles comprising a first, second, third and fourth stage-specific separation profile comprising stage-specific protein and protein complex clusters representing, respectively, stage I, II III or IV of breast cancer,
   wherein:
   (i) a substantial similarity of the test separation profile to the first stage-specific separation profile indicates that the subject has stage I breast cancer:
   (ii) a substantial similarity of the test separation profile to the first stage-specific separation profile indicates that the subject has stage II breast cancer;
   (iii) a substantial similarity of the test separation profile to the first stage-specific separation profile indicates that the subject has stage III breast cancer;
   (iv) a substantial similarity of the test separation profile to the first stage-specific separation profile indicates that the subject has stage IV breast cancer.

26. The method of claim 25, wherein the biological sample comprises a biological fluid.

27. The method of claim 26, wherein the biological fluid is selected from the group consisting of blood, serum, saliva, urine, lymph, perspiration, mucus, cerebro-spinal fluid, lachrymal fluid, vitreous humor, semen, vaginal secretions, and mammary gland secretions.

28. The method of claim 25, wherein the biological sample comprises the hydrophobic fraction of a biological fluid.

29. The method of claim 25, wherein the biological sample comprises the hydrophilic fraction of a biological fluid.

30. A method of determining the prognosis of a subject with breast cancer, comprising determining the stage of breast cancer in the subject according to claim 25, wherein the prognosis of the subject decreases with increasing breast cancer stage.

31. The method of any one of claims 1, 9, 18 or 25, wherein said comparing is conducted side-by-side.

32. The method of claim 9, 18 or 25, wherein said standard separation profile comprises disease specific markers that have been identified by the method of claim 1.

* * * * *